US008152750B2

(12) United States Patent
Vournakis et al.

(10) Patent No.: US 8,152,750 B2
(45) Date of Patent: Apr. 10, 2012

(54) VASCULAR ACCESS PRESERVATION IN HEMODIALYSIS PATIENTS

(75) Inventors: John N. Vournakis, Charleston, SC (US); Sergio Finkielsztein, Newton, MA (US)

(73) Assignee: Marine Polymer Technologies, Inc., Danvers, MA (US)

( * ) Notice: Subject to any disclaimer, the term of this patent is extended or adjusted under 35 U.S.C. 154(b) by 0 days.

(21) Appl. No.: 10/940,473

(22) Filed: Sep. 13, 2004

(65) Prior Publication Data

US 2005/0075597 A1 Apr. 7, 2005

Related U.S. Application Data

(60) Provisional application No. 60/502,878, filed on Sep. 12, 2003.

(51) Int. Cl.
*A61M 37/00* (2006.01)
*A61F 13/00* (2006.01)
*A61B 5/02* (2006.01)

(52) U.S. Cl. ............ 604/4.01; 602/48; 602/49; 602/50; 602/52; 602/53; 600/490; 604/304

(58) Field of Classification Search .................. 604/4.01, 604/5.01–5.04, 6.05, 6.06, 6.07, 6.16, 1, 604/2, 304; 128/898; 424/400, 422–426, 424/443–449, 78.08, 520, 529–533; 514/55, 514/801, 807, 834, 903; 600/490; 602/48, 602/49, 50, 52, 53
See application file for complete search history.

(56) References Cited

U.S. PATENT DOCUMENTS

| 3,232,836 | A | * | 2/1966 | Carlozzi et al. | 514/62 |
| 3,903,268 | A | * | 9/1975 | Balassa | 514/55 |
| 4,394,373 | A | | 7/1983 | Malette et al. | |
| 4,651,725 | A | * | 3/1987 | Kifune et al. | 602/49 |
| 5,437,292 | A | * | 8/1995 | Kipshidze et al. | 128/898 |
| 5,510,102 | A | | 4/1996 | Cochrum | |
| 5,622,834 | A | * | 4/1997 | Vournakis et al. | 435/84 |
| 5,623,064 | A | | 4/1997 | Vournakis et al. | |
| 5,624,679 | A | * | 4/1997 | Vournakis et al. | 424/444 |
| 5,635,493 | A | * | 6/1997 | Vournakis et al. | 514/55 |
| 5,686,115 | A | | 11/1997 | Vournakis et al. | |
| 5,763,411 | A | * | 6/1998 | Edwardson et al. | 514/21 |
| 5,804,428 | A | * | 9/1998 | Edwardson et al. | 435/212 |
| 5,846,952 | A | | 12/1998 | Vournakis et al. | |
| 5,858,350 | A | | 1/1999 | Vournakis et al. | |
| 5,990,079 | A | * | 11/1999 | Wolf et al. | 514/13.7 |
| 6,063,911 | A | | 5/2000 | Vournakis et al. | |
| 6,599,720 | B2 | | 7/2003 | Vournakis et al. | |
| 6,610,668 | B2 | | 8/2003 | Vournakis et al. | |
| 6,630,459 | B2 | | 10/2003 | Vournakis et al. | |
| 6,649,599 | B2 | | 11/2003 | Vournakis et al. | |
| 6,686,342 | B2 | | 2/2004 | Vournakis et al. | |
| 6,693,188 | B2 | * | 2/2004 | Bohlmann et al. | 536/55.2 |
| 6,743,783 | B1 | | 6/2004 | Vournakis et al. | |
| 7,115,588 | B2 | * | 10/2006 | Vournakis et al. | 514/62 |
| 7,175,646 | B2 | * | 2/2007 | Brenneman et al. | 606/213 |
| 7,931,637 | B2 | * | 4/2011 | Vournakis et al. | 604/389 |
| 2002/0019367 | A1 | | 2/2002 | Vournakis et al. | |
| 2002/0071855 | A1 | * | 6/2002 | Sadozai et al. | 424/426 |
| 2002/0197302 | A1 | * | 12/2002 | Cochrum et al. | 424/445 |
| 2003/0078234 | A1 | * | 4/2003 | Vournakis et al. | 514/54 |
| 2004/0087015 | A1 | | 5/2004 | Vournakis et al. | |
| 2004/0237970 | A1 | * | 12/2004 | Vournakis et al. | 128/898 |
| 2004/0243043 | A1 | * | 12/2004 | McCarthy et al. | 602/46 |
| 2005/0004072 | A1 | | 1/2005 | Vournakis et al. | |

FOREIGN PATENT DOCUMENTS

| JP | 2000-186048 A | 4/2000 |
| WO | WO 95/15343 | 6/1995 |
| WO | WO 96/39122 | 12/1996 |
| WO | WO 00/36918 | 6/2000 |
| WO | WO 02/22059 A1 | 3/2002 |
| WO | WO 02/24239 A1 | 3/2002 |
| WO | WO 02/063961 | 8/2002 |
| WO | WO 2004/060172 | 7/2004 |
| WO | WO 2004/060172 A1 * | 7/2004 |
| WO | WO 2004/076637 | 9/2004 |

OTHER PUBLICATIONS

Vaziri et al., Control of Bleeding From Cannulation Sites With Topical Thrombi in Dialyzed Patients, 1978, Journal of Dialysis, vol. 2/No. 4, 393-398.*
Kipshidze, et al., Percutaneous Application of Fribrin Sealant to Achieve Hemostasis Following Arterial Catheterization, The Journal of Invasive Cardiology, 1998, vol. 10, No. 3, 133-141.*
Astor et al., 2002, "Race-specific association of lipoprotein(a) with vascular access interventions in hemodialysis patients: the Choice Study," Kidney Int. 61(3):1115-1123.
Berkoben, 1995, "Maintenance of permanent hemodialysis vascular access patency," Anna J. 22(1):17-24.
Brothers et al., 1996, "Failure of dialysis access: revise or replace?" J. Surg. Res. 60(2):312-316.
Butterly, 1994, "A quality improvement program for hemodialysis vascular access," Adv. Ren. Replace. Ther. 1(2):163-166.
Camenzind et al., 1994, "Collagen application versus manual compression: a prospective randomized trial for arterial puncture site closure after coronary angioplasty," J. Am. Coll. Cardiol. 24(3):655-662.

(Continued)

*Primary Examiner* — Tatyana Zalukaeva
*Assistant Examiner* — Ginger T Chapman
(74) *Attorney, Agent, or Firm* — Jones Day

(57) ABSTRACT

The present invention relates generally to the field of hemodialysis, including methods and kits that can be employed to improve hemodialysis therapy. The present invention encompasses methods and kits useful for reducing vascular access complications associated with hemodialysis therapy and prolonging the period of time for which a vascular access site can be used in a patient.

34 Claims, No Drawings

OTHER PUBLICATIONS

Di Minno et al., 1985, "Platelet dysfunction in uremia. Multifaceted defect partially corrected by dialysis," Am. J. Med. 79(5):552-559.
Falstrom et al., 1997, "Reduction of femoral artery bleeding post catheterization using a collagen fibrin sealant," Cathet. Cardiovasc. Diagn. 41(1):79-84.
Goldwasser, 1994, "Correlates of vascular access occlusion in hemodialysis," Am. J. Kidney Dis. 24(5):785-794.
Gwechenberger et al., 1997, "Use of a collagen plug versus manual compression for sealing arterial puncture site after cardiac catheterization," Angiology 48(2):121-126.
Hakim et al., 1998, "Hemodialysis access failure: a call to action," Kidney Int. 54(4):1029-1040.
Harland, 1994, "Placement of permanent vascular access devices: surgical considerations," Adv. Ren. Replace. Ther. 1(2):99-106.
Hoekstra et al., 1998, "Percutaneous microcrystalline chitosan application for sealing arterial puncture sites," Biomaterials 19(16):1467-1471.
Ismail et al., 1995, "Reduction of femoral arterial bleeding post catheterization using percutaneous application of fibrin sealant," Cathet. Cardiovasc. Diagn. 34(1):88-95.
Kipshidze et al., 1998, "Percutaneous Application of Fibrin Sealant to Achieve Hemostasis Following Arterial Catheterization," J. Invasive. Cardiol. 10(3):133-141.
Mayers, 1992, "Vascular access surgery for maintenance hemodialysis. Variables in hospital stay," Asaio J. 38(2):113-115.
Merino et al., 1992, "Percutaneous vascular hemostasis device for interventional procedures," Cathet. Cardiovasc. Diagn. 26(4):319-322.
Prior et al., 2000, "Efficacy of a novel hemostatic agent in animal models of impaired hemostasis," J. Biomed. Mater. Res. 53(3):252-257.
Sanborn et al., 1993, "A multicenter randomized trial comparing a percutaneous collagen hemostasis device with conventional manual compression after diagnostic angiography and angioplasty," J. Am. Coll. Cardiol. 22(5):1273-1279.
Schwab, 1999, "Vascular access for hemodialysis," Kidney Int. 55(5):2078-2090.
Schwab, 1989, "Prevention of hemodialysis fistula thrombosis. Early detection of venous stenoses," Kidney Int. 36(4):707-711.
Solomonson, 1994, "Risk factors in patients having surgery to create an arteriovenous fistula," Anesth. Analg. 79(4):694-700.
Spergel, 1997, "Issues in Vascular Access. Improving outcomes in the face of managed care and capitation: one surgeons perspective," Nephrol. News Issues 11(3):26-27, 35.
Vaziri, 1979, "Topical thrombin and control of bleeding from the fistula puncture sites in dialyzed patients," Nephron 24(5):254-256.
Varizi et al., 1978, "Control of bleeding from cannulation sites with topical thrombin in dialyzed patients," J. Dial. 2(4):393-398.
Windus, 1997, "Effects of antiplatelet drugs on dialysis-associated platelet deposition in polytetrafluoroethylene grafts," Am. J. Kidney Dis. 29(4):560-564.
O'shea et al. Hypercoagulable states and antithrombotic strategies in recurrent vascular access site thrombosis. J Vasc Surg. Sep. 2003;38(3):541-8.
Sands et al. Antibodies to prothrombin, factor V, and beta2-glycoprotein I and vascular access thrombosis. ASAIO J. Sep.-Oct. 2001;47(5):507-10.
Sands et al. Antibodies to topical bovine thrombin correlate with access thrombosis. Am J Kidney Dis. May 2000;35(5):796-801.
Feldman et al., 1993, "Hemodialysis vascular access morbidity in the United States," Kidney International 43:1091-1096.
Jewelewicz et al., 2003, "Modified rapid deployment hemostat bandage reduces blood loss and mortality in coagulopathic pigs with severe liver injury," J Trauma 55(2):275-281.
Meyer et al., 1999, "Control of post dialysis bleeding in patients on chronic oral anticoagulation therapy," J Am Soc Nephrol 10:212A, Abtract A1078.
Nader et al., 2002, "Clinical evaluation of the SyvekPatch® in consecutive patients undergoing interventional, EPS and diagnostic cardiac catheterization procedures," J Invas Cardiol 14(6):305-307.
Najjar et al., 2004, "Evaluation of poly-N-acetyl glucosamine as a hemostatic agent in patients undergoing cardiac catheterization: a double-blind, randomized study," J Trauma 57:S38-S41.
Schwaitzberg et al., 2004, "Comparison of poly-N-acetyl glucosamine with commercially available topical hemostats for achieving hemostasis in coagulopathic models of splenic hemorrhage," J Trauma 57:S29-S32.
Shubrooks et al., 2000, "Earlier ambulation at 2 hours following cardiac catheterization using Syvek Patch®," SCA&I 2000 Meeting Abstracts 143, Abstract PO22.
New Yakurigaku (Pharmacology) (fourth edition), 2002, pp. 408-409.
Unalp et al., 2009, "Does Poly-N-Acetyl Glucosamine Patch Use Reduce Arteriovenous Fistula and Graft Failure Rates in Hemodialysis Patients With End-Stage Renal Disease?" Amer. J. Med. Sci. 338(3):178-184.
Chan et al., 2000, "Comparison of Poly-N-acetyl Glucosamine (P-GlcNAc) with Absorbable Collagen (Actifoam), and Fibrin Sealant (Bolheal) for Achieving Hemostasis in a Swine Model of Splenic Hemorrhage," J. Trauma: Injury, Infection, and Critical Care 48(3):454-458.
Cole et al., 1999, "A Pilot Study Evaluating the Efficacy of a Fully Acetylated Poly-N-acetyl Glucosamine Membrane Formulation as a Topical Hemostatic Agent," Surgery 126(3):510-517.
Sands et al., "Antibodies to topical bovine thrombin correlate with access thrombosis," 2000, Am J. of Kidney Diseases 35(5): 796-801.
Syvek Patch Product Insert (in use from Jul. 1999).
Syvek Patch Product Insert revision 01 (in use from Jul. 2000).
Syvek Patch Product Insert revision 02 (in use from Jun. 2001).
Syvek Patch Product Insert revision 03 (in use from Apr. 2002).
Syvek Patch Product Insert revision 04 (in use from Sep. 2005).
Lundblad et al., A Review of the Therapeutic Uses of Thremkin; Thromb. Haemost. May; 91(5): 851-860.

* cited by examiner

VASCULAR ACCESS PRESERVATION IN HEMODIALYSIS PATIENTS

This application claims priority to U.S. Provisional Application Ser. No. 60/502,878, filed Sep. 12, 2003, which is incorporated herein by reference in its entirety.

1. INTRODUCTION

The present invention relates generally to the field of hemodialysis, including methods and kits that can be employed to improve hemodialysis therapy. More specifically, the present invention relates to methods for reducing short-term and/or long-term vascular access complications associated with hemodialysis therapy, for example reducing the average number of vascular access interactions associated with a hemodialysis therapy, decreasing an infection rate associated with hemodialysis therapy, or preserving access to a hemodialysis vascular access site by reducing the time of compression applied to a vascular access site to about one to about fourteen minutes, for the majority of hemodialysis sessions. The present invention also provides for a kit comprising a composition and instructions for achieving a reduction in vascular access complications associated with hemodialysis therapy for example, a reduction in the average number of intreventions to replace or repair vascular access sites, a decrease in infection rate associated with hemodialysis therapy, or a preservation of access to a hemodialysis vascular access site.

2. BACKGROUND

Maintenance hemodialysis for end stage renal disease (ESRD) patients requires a reliable means of repetitive access to large blood vessels that are capable of rendering rapid extracorporeal blood flow to an artificial kidney. Typically an artery and vein are sutured to form a fistulae which enlarges to a point of maturity over several months. Synthetic grafts are also used.

Hemodialysis patients receiving dialysis treatment via native vein arteriovenous fistulae and synthetic grafts typically undergo puncture of skin, subcutaneous tissue, and vascular access with 14-17 gauge needles two to three times weekly. When the procedure is finished and the needles are removed from the skin, many patients bleed from the puncture site for an extended period of time such that the standard treatment involves post-hemodialysis compression at the site for at least 15-20 minutes.

Problems are commonly associated with repeated vascular access, i.e., access to circulation, and include hyperplasia, thrombosis, hematoma, venous stenosis, arterial stenosis, vascular occlusion, infection, and morbidity. Thrombosis, i.e., a blood clot, is the primary cause of access failure responsible for 50% of cases in polytetraflouroethylene (PTFE) grafts. In those situations where anatomic lesions can be identified, the pathology has been found to be intimal hyperplasia. Other causes of vascular access complications include: venous or arterial stenosis and infection (Mayers 1992, ASAIO J. 38:113-115). These complications with vascular access sites lead to blocking or narrowing of vascular access sites which in turn result in an increased incidence of surgery to repair, replace, or create new vascular access sites. Degradation of the vascular access site also results in a reduction in the delivered dose of dialysis through the use of temporary catheters or reduced blood flow (Hakim and Himmelfarb, 1998, Kidney International, 54:1029-1040). Schwab found that 30% of hemodialysis patients with A-V fistulae, allowed to mature for 60 days, required intervention after about 800 days of hemodialysis therapy, and 80% of hemodialysis patients with A-V grafts required intervention after about 800 days of hemodialysis therapy. After 400 days of hemodialysis therapy, about 18% of A-V fistulae patients and 50% of A-V graft patients required intervention, and after about 200 days 10% of A-V fistulae and 30% of A-V graft patients required intervention (Schwab, 1999, Kidney International, 55:2078-2090).

Hemodialysis vascular access is also a major risk factor for infection and bacteremia, caused mostly by staphylococcal organisms, such as, but not limited to, *S. taphylococcus aureus* and *Enterococcus* spp. (Nassar and Ayus, 2001, Kidney International 60:1-13; Tokars et al., 2002, AJIC 30:288-295). These infections and bacteremia lead to complications such as degradation in vascular access sites and surgical replacement of vascular access sites. Other complications can include infectious endocarditis, septic arthritis, epidural abscess, septic pulmonary emboli, and osteomyelitis. Infections and bacteremia can be clinically diagnosed or a leukocyte-labeled indium scan of the vascular access site can be performed to identify infection where clinical manifestation of infection is not apparent or definite. One skilled in the art would know how to perform such scans and identify infections or resulting vascular access complications.

The pathology and risk factors for vascular access complications have been studied. Age, diabetes, the use of synthetic grafts, serum levels of liproprotein(a) (Lp(a))$\geq$57 mg/dL, serum fibronectin, calcification, apolipoprotein(a) serum levels, excessive compression of the vascular access site following hemodialysis or during sleep, turbulent blood flow and reduced blood pressure have been identified as predisposing to access occlusion (Berkoben, 1995, ANNA J. 22:17-24; Butterly, 1994, Adv. Ren Rep. Thpy. 1: 163-166; Goldwasser 1994, AJKD 24:785-794; Astor et al., 2002, Kidney International 61:1115-1123). The cause of vascular access complications is suggested to be multifactorial and poorly understood (Goldwasser, 1994, AJKD 24:785-794; Schwab, 1989, Kidney International, 36:707-711; and Windus, 1997, AJKD 29(4):560-564).

Hemodialysis patients also have an increased bleeding tendency due to platelet dysfunction and ineffective platelet-vessel interaction induced by uremia. In hemodialysis patients, the risk of prolonged bleeding is further increased by systematic anticoagulation resulting from the continuous infusion of heparin during the dialysis procedure (Di Minno et al., 1985, Am. J. Med. 79:552-559). Many of these patients have a high incidence of cardiovascular risk factors. A retrospective study done by the Department of Anesthesiology of the Mayo Clinic reported that for all the patients requiring creation of an A-V fistula in the years 1986 to 1991, 92% suffered from hypertension, 86% from coronary artery disease and 42% from a previous myocardial infarction (Solomonson, 1994, Anesth. Analg. 79:694-700). Most of this group of patients must be on prophylactic anticoagulation therapy with aspirin or warfarin. Further, thiazide diuretics, which are commonly used to treat hypertension or congestive heart failure, impair megakaryocyte production and can produce mild thrombocytopenia which may persist for several months after the drug is discontinued (Harrison's Principles of Internal Medicine 13th Ed. 1994, p.1799).

Hemostasis, i.e., the stopping or cessation of bleeding, is often compromised in hemodialysis patients. The abnormal hemostasis associated with ESRD patients is most apparent in the prolonged post treatment bleeding. Traditionally, when the cannulation needles are removed at the end of treatment, many hemodialysis patients require long compression times at the site of removal to stop bleeding. Hemostasis is typically obtained by 15-20 minutes of manual compression (Schwab, 1994, Kidney International 36:707-711). Vaziri reported that in the population of heparinizied ESDR patients studied the mean bleeding time was about 7-9 minutes following hemodialysis which was reduced to about 3.2-3.3 minutes with the topical administration of bovine thrombin to the site where the hemodialysis needles are removed (Varizi et al., 1978, Journal of Dialysis, 2:393-398; and Varizi, 1979, Nephron 24:254-256).

Several compositions that can act as hemostatic agents and typically include collagen or fibrin are known (Falstrom et al., 1997, Catheterization and Cardiovasular Diagnosis 41:79-84; Hoekstra et al., 1998, Biomaterials. 19:1467-1471; Prior et al., 2000, Journal of Biomedical Materials Research. 53(3): 252-257). U.S. Pat. No. 4,394,373, for example, discloses compositions that act as coagulants and may be used to promote clotting of a wound by placing the compositions in contact with the wound where the composition comprises liquid or powder chitosan. U.S. Pat. No. 5,510,102, for example, discloses compositions that act as coagulants and may be used to promote clotting of a wound by placing the compositions in contact with the wound where the composition comprises platelet rich plasma plus a biocompatible polymer that is a hemostatic agent such as alginate. The compositions of U.S. Pat. Nos. 4,394,373 and 5,510,102 are either applied directly to the wound surface, in the case of treatment of a superficial wound or in the case of a puncture in an artery left by a needle or catheter.

Preserving access function and long-term vascular access is essential for the care of dialysis patients, particularly now that high-efficiency dialysis places even more demands on access function, and with increasing numbers of older, sicker patients entering the ESRD program with limited access sites. Vascular access complications remain the single greatest cause of morbidity and account for approximately one third of all admissions and hospitalization days in the hemodialysis population (Spergel, 1997, Neph. News and Issues. 3:26-27, 35). An average 1.2-2.8 surgical procedures per patient are performed each year to repair or replace the vascular access site (Brothers et al., 1996, J. Sur. Research 60:312-316; Harland, 1994, Adv. Ren. Rep Therapy 1:99-106). As much as $1 billion annually is spent on placement and maintenance of vascular access (Spergel, 1997; Hakim and Himmelfarb, 1998, Kidney International, 54:1029-1040).

High rates of vascular access complications in the hemodialysis population coupled with the increased use of high flux dialyzers, which require higher blood flow, draw attention to the need for new methods for maintaining blood flow through vascular access sites (Hakim and Himmelfarb, 1998, Kidney International, 54:1029-1040).

The patents and published articles referenced in this section are incorporated by reference herein in their entirety.

3. SUMMARY

The advantages of the methods of the invention over the existing traditional methods include, for example, the reduction in short-term and/or long-term vascular access complications, a reduction in the number of interventions to repair or replace a vascular access site, and the increase in the length of time a vascular access site remains viable for hemodialysis therapy.

In one aspect, the invention provides for a method for reducing vascular access complications associated with a hemodialysis therapy in a patient comprising applying topically to a hemodialysis vascular access site during a hemodialysis session a composition comprising an amount of a vasoconstrictor or coagulant effective for reducing or ceasing post-hemodialysis bleeding at the vascular access site, and applying compression to the hemodialysis vascular access site for a period of about one to about fourteen minutes. In another aspect, the invention provides for a method for reducing vascular access complications associated with a hemodialysis therapy in a patient comprising applying topically to a hemodialysis vascular access site during a hemodialysis session a composition comprising a barrier-forming material effective for reducing or ceasing post-hemodialysis bleeding in comparison to gauze alone at the vascular access site, and applying compression to the hemodialysis vascular access site for a period of about one to fourteen minutes. In another aspect, the invention provides for a method for reducing the average number of interventions to repair or replace vascular access sites in a hemodialysis patient comprising applying topically to a hemodialysis vascular access site during a hemodialysis session a composition comprising an amount of a vasoconstrictor or coagulant effective for reducing or ceasing post-hemodialysis bleeding at the vascular access site, and applying compression to the hemodialysis vascular access site for a period of about one to fourteen minutes. In another aspect, the invention provides for a method for decreasing an infection rate associated with a hemodialysis therapy in a patient comprising applying topically to a hemodialysis vascular access site during a hemodialysis session a composition comprising an amount of a vasoconstrictor or coagulant effective for reducing post-hemodialysis bleeding at the vascular access site, and applying compression to the hemodialysis vascular access site for a period of about one to fourteen minutes. In another aspect, the invention provides for a method for preserving access to a hemodialysis vascular access site associated with a hemodialysis therapy in a patient comprising applying topically to a hemodialysis vascular access site during a hemodialysis session a composition comprising an amount of a vasoconstrictor or coagulant effective for reducing or ceasing post-hemodialysis bleeding at the vascular access site, and applying compression to the hemodialysis vascular access site for a period of about one to fourteen minutes.

In certain embodiments of the methods of the invention, compression is applied to the vascular access site for a period of about one to about fourteen minutes for multiple sessions of the hemodialysis sessions of the therapy, preferably for the majority of hemodialysis sessions of the therapy, and the number of vascular access complications associated with the hemodialysis therapy is reduced in comparison to hemodialysis patients for whom compression is applied for a period of greater than about fourteen minutes for the majority of a comparable number of hemodialysis sessions. In certain embodiments of the methods of the invention, the vascular access complications are long-term, such as, but not limited to, hyperplasia, thrombosis, venous stenosis, arterial stenosis and/or morbidity. In certain embodiments, the vascular access complications are short-term, such as, but not limited to, hematomas and/or infections.

In certain embodiments, the composition comprises a coagulant. In other embodiments, the composition comprises a vasoconstrictor. In yet other embodiments, the composition comprises a coagulant and a vasoconstrictor.

In certain embodiments, the vascular access complication reduced or ceased by the methods and/or kits of the invention is hyperplasia, thrombosis, hematoma, venous stenosis, arterial stenosis, or infection. In particular embodiments, failure of vascular access sites due to thrombosis is reduced to fewer than 80% of patients having vascular access complications. In particular embodiments, failure of vascular access sites due to venous stenosis is reduced to fewer than 80% of patients having vascular access complicaitons. In particular embodiments, failure of vascular access sites due to arterial stenosis is reduced to fewer than 2% of patients having vascular access complications. In particular embodiments, failure of vascular access sites due to infection is reduced to fewer than 15% of patients having vascular access complications. In other embodiments, failure of vascular access sites due to infection is reduced to fewer than 20% of patients having vascular access complications. In certain embodiments of the methods and kits of the invention where the patient has a mature A-V fistulae, vascular access complicaitons are reduced by about 10% in number or severity after about 200 days of hemodialysis therapy by about 20% in number or severity after about 500 days of hemodialysis therapy, or by about 30% in number or severity after about 800 days of therapy, relative to compression without coagulant or vasoconstrictor (e.g., compression with gauze alone). In certain embodiments of the methods and kits of the invention where the patient has a mature A-V graft, vascular access complications are reduced to by about 20% in number or severity after about 100 days of hemodialysis therapy, by about 35% in number or severity after about 200 days of hemodialysis therapy, or by about 50% in number or severity after about 500 days of therapy, relative to compression without coagulant or vasoconstrictor (e.g., compression with gauze alone).

In certain embodiments of the methods and kits of the invention, the methods of the invention further comprise the proviso that the patient is not concurrently treated with erythropoietin. The erythropoietin may be EPOGEN™. In embodiments where the patient is not concurrently treated with erythropoietin, this means that the patient has not received erythropoietin for preferably about 1 week, 2 weeks, 3 weeks, 4 weeks, 1.5 months, 2 months, 2.5 months, 3 months, 3.5 months, 4 months, 5, months, 6 months, 7 months, 8 months, 9 months, 10 months 11 months or 12 months prior to initiation of therapeutic regimens of the invention. In certain embodiments of the methods and kits of the invention, wherein erythropoietin is administered to the patient in conjunction with practicing the methods of the invention, the amount of erythropoietin is reduced in comparison to hemodialysis patients for whom compression is applied for a period of greater than about fourteen minutes for the majority of hemodialysis sessions. In related embodiments of the methods and kits of the invention, the erythropoietin administered comprises less than about 3,000 units per dose, or as a total of multiple doses, of recombinant erythropoietin or epoetin alfa.

In certain embodiments of the methods and kits of the invention, the vascular access complication is reduced blood flow through the hemodialysis vascular access site relative to a newly matured vascular access site. In related embodiments, the blood flow is measured in the newly matured vascular access site prior to any hemodialysis use. In related embodiments, the blood flow is measured in the newly matured vascular access site in the patient prior to any hemodialysis use. In certain embodiments of the methods and kits of the invention, the vascular access complication is reduced blood flow through the hemodialysis vascular access site relative to the average blood flow through a newly matured vascular access site. In one embodiment, the average blood flow is the average flow for newly matured vascular access sites in ESRD patients.

In another aspect, the invention provides for a method for reducing vascular access complications associated with a hemodialysis therapy in a patient comprising applying topically to a hemodialysis vascular access site during a hemodialysis session a composition comprising a barrier-forming material effective for reducing or ceasing post-hemodialysis bleeding at the vascular access site in comparison to gauze alone; and applying compression to the hemodialysis vascular access site for a period of about one to about fourteen minutes, wherein such compression is applied to the hemodialysis vascular access site for a period of about one to about fourteen minutes for multiple sessions of the hemodialysis sessions of the therapy, preferably for the majority of hemodialysis sessions of the therapy, and the number of vascular access complications associated with the hemodialysis therapy is reduced in comparison to hemodialysis patients for whom compression is applied for a period of greater than about fourteen minutes for the majority of hemodialysis sessions. In certain embodiments, the composition comprises a coagulant. In other embodiments, the composition comprises a vasoconstrictor. In yet other embodiments, the composition comprises a coagulant and a vasoconstrictor. In yet other embodiments, the composition comprises collagen. In still other embodiments, the composition of the method and kits of the invention comprises a vasconstrictor, coagulant, and/or barrier-forming material, with the proviso that the composition does not comprise collagen.

In yet another aspect, the invention provides for a method for reducing the average number of interventions to surgically repair or replace vascular access sites in a hemodialysis patient comprising applying topically to a hemodialysis vascular access site during a hemodialysis session a composition comprising an amount of a vasoconstrictor or coagulant effective for reducing or ceasing post-hemodialysis bleeding at the vascular access site; and applying compression to the hemodialysis vascular access site for a period of about one to fourteen minutes, wherein such compression is applied for about one to about fourteen minutes for multiple sessions of the hemodialysis sessions of the therapy, preferably for the majority of hemodialysis sessions of a hemodialysis therapy, and the average number of interventions to replace or repair vascular access sites is reduced in comparison to hemodialysis patients for whom compression is applied for a period greater than about fourteen minutes for the majority of hemodialysis sessions. In certain embodiments, the composition comprises a coagulant. In other embodiments, the composition comprises a vasoconstrictor. In yet other embodiments, the composition comprises a coagulant and a vasoconstrictor.

In embodiments of the methods and kits of the invention, the intervention comprises surgery to repair or replace a vascular access site. In one embodiment, the average number of interventions is fewer than about 2.8 per year. In another embodiment, the average number of interventions is fewer than about 2.0 per year. In yet another embodiment, the average number of interventions is fewer than about 1.2 per year.

In another aspect, the invention also provides for a method for decreasing an infection rate associated with a hemodialysis therapy in a patient comprising applying topically to a hemodialysis vascular access site during a hemodialysis session a composition comprising an amount of a vasoconstrictor or coagulant effective for reducing post-hemodialysis bleeding at the vascular access site; and applying compression to the hemodialysis vascular access site for a period of about one to fourteen minutes, wherein such compression is applied for about one to about fourteen minutes for multiple sessions of the hemodialysis sessions of the therapy, preferably for the majority of hemodialysis sessions of the therapy, and the rate of infection associated with hemodialysis decreases in comparison to hemodialysis treatments in patients for whom compression is applied for a period greater than about fourteen minutes for the majority of hemodialysis sessions. In certain embodiments, the composition comprises a coagulant. In other embodiments, the composition comprises a vasoconstrictor. In yet other embodiments, the composition comprises a coagulant and a vasoconstrictor. In certain embodiments, the vascular access complications due to infection reduced by about 15% in number or severity, relative to compression without coagulant or vasoconstrictor (e.g., compression with gauze alone). According to certain aspects of the invention, the infection is HIV, Hepatitis C, macrolides, lincomycin, vancomycin resistant enterococcus, or streptogramin B (MLS resistance). In one aspect of the invention, the composition further comprises an anti-fungal, anti-viral, or antibacterial agent.

The invention further provides for a method for preserving access to a hemodialysis vascular access site associated with a hemodialysis therapy in a patient comprising applying topically to a hemodialysis vascular access site during a hemodialysis session a composition comprising an amount of a vasoconstrictor or coagulant effective for reducing or ceasing post-hemodialysis bleeding at the vascular access site; and applying compression to the hemodialysis vascular access site for a period of about one to about fourteen minutes, wherein such cessation compression is applied for about one to about fourteen minutes for multiple sessions of the hemodialysis sessions of the therapy, preferably for the majority of hemodialysis sessions of the therapy, and the access to the hemodialysis vascular access site is preserved in comparison to hemodialysis patients for whom compression is applied for a period greater than about fourteen minutes for the majority of hemodialysis sessions. In certain embodiments, the composition comprises a coagulant. In other embodiments, the composition comprises a vasoconstrictor. In yet other embodiments, the composition comprises a coagulant and a vasoconstrictor.

In certain embodiments of the invention, an effective amount of a vasoconstrictor and/or coagulant is an amount that results in reduction or cessation of bleeding when applied to a catheter exits wound without compression. In other embodiments of the invention, an effective amount of a vasoconstrictor and/or coagulant is an amount that results in reduction or cessation of bleeding when applied to a catheter exits wound with compression according to the methods of the invention.

In certain embodiments, the methods of the invention are practiced in the first hemodialysis session the patient undergoes. In related embodiments, the methods of the invention are practiced in all of the hemodialysis session the patient undergoes. In still other embodiments, the patient has not had any hemodialysis sessions prior to initiating a therapeutic regimen of the invention. In still other embodiments, the patient has had about 1, 2, 3, 4, 5, 6, 7, 8, 9, 10, 12, 14, 16, 18, 20, 25, 30, 35, 40, 45, or 50 hemodialysis sessions where the methods of the invention were not used or compression was applied for about 10, 11, 12, 13, or 14 minutes or greater. In certain embodiments, the methods of the invention are practiced on the patient for about 3 months, 6 months, 1 year, 1.5 years, 2 years, 2.5 years, 3 years, 4 years, 5 years, 6 years, 7 years, 8 years, 9 years, 10 years, 11 years, or 15 years.

In certain embodiments of the methods and kits of the invention described herein, the therapeutic regimens of the invention are at least ten months in duration.

In certain embodiments of the methods and kits of the invention described herein, the vasoconstrictor or coagulant is substantially free of allergens or is non-immunogenic. In related embodiments, the vasoconstrictor or coagulant does not comprise bovine derived thrombin.

In preferred embodiments of the methods and kits of the invention described herein, the therapeutic regimen of the invention entails maintaining compression for about one to five minutes in conjunction with topical application of a vasoconstrictor or coagulant and this procedure is preferably repeated, preferably for the majority of hemodialysis sessions of the therapy. In another preferred embodiment of the methods and kits of the invention described herein, the compression is maintained for about one to ten minutes for the majority of hemodialysis sessions of the therapy.

In certain embodiments of the methods and kits of the invention described herein, the coagulant comprises alpha-2-antiplasmin, alpha-1-antitrypsin, alpha-2-macroglobulin, aminohexanoic acid, aprotinin, a source of calcium ions, calcium alginate, calcium-sodium alginate, casein kinase II, chitin, chitosan, collagen, cyanoacrylates, epsilon-aminocaproic acid, Factor XIII, fibrin, fibrin glue, fibrinogen, fibronectin, gelatin, living platelets, metha-crylates, PAI-1, PAI-2, plasmin activator inhibitor, p-GlcNAc, plasminogen, platelet agonists, protamine sulfate, prothrombin, an RGD peptide, sphingosine, a sphingosine derivative, thrombin, thromboplastin, or tranexamic acid.

In certain embodiments of the methods and kits of the invention described herein, the vasoconstrictor is adrenaline, endothelin-1, epinephrine, phenylephrine, serotonin, thromboxane, or U-46619.

In certain embodiments of the methods and kits of the invention described herein, the composition further comprises collagen.

In one aspect of the methods and kits of the invention described herein, the composition further comprises a pharmaceutical carrier.

In certain embodiments of the methods and kits of the invention described herein, the hemodialysis vascular access site comprises a vein sutured to an artery. In related embodiments of the methods and kits of the invention described herein, the hemodialysis vascular access site comprises a native arteriovenous fistula. In other embodiments of the methods and kits of the invention described herein, the hemodialysis vascular access site comprises a synthetic vascular graft.

In certain embodiments of the methods and kits of the invention described herein, the therapeutic regimens of the invention are practiced two or three times per week.

In certain embodiments of the methods of the invention described herein, before applying topically to a hemodialysis vascular access site during a hemodialysis session a composition of the invention in conjunction with compression, an anticoagulant is administered to the patient. In related embodiments of the methods of the invention described herein, the anticoagulant is selected from the group consisting of coumadin, heparin, nadroparin, asparin, and a thrombolytic agent. In yet other related embodiments of the methods of the invention described herein, the composition further comprises protamine sulfate in an amount effective to neutralize heparin.

In certain embodiments of the methods of the invention described herein, the compression is manual compression. In related embodiments of the methods of the invention described herein, the compression is not occlusive and blood flow continues in the vascular access site. In other embodiments of the methods of the invention described herein, the compression is mechanical compression. In certain embodiments of the methods of the invention described herein, the compression is applied to a vein or artery proximal of the hemodialysis vascular access site. In embodiments of the methods of the invention described herein, the compression is applied with a compression bandage.

According to one aspect of the methods of the invention described herein, the composition is formulated as a gel, solid, liquid, sponge, foam, spray, emulsion, suspension, film, membrane, mat, string, microbead, microsphere, microfibril, or solution. In certain embodiments of the methods of the invention described herein, the composition further comprises a neutral liquid, neutral gel or neutral solid. In preferred embodiments the neutral solid comprises a gauze, a bandage, or a barrier-forming material. In other preferred embodiments, the neutral solid is a gauze. In related embodiments of the methods of the invention described herein, the film, membrane, or mat comprises a barrier-forming material. In certain embodiments of the methods of the invention described herein, the composition is in the form of a coating on the neutral solid.

In certain embodiments of the methods of the invention described herein, the hemodialysis is administered using lumen canulation needles that are fewer than 15 gauge.

In certain embodiments of the methods of the invention described herein, the patient is a human. In other embodiments, the patient is diabetic. In other embodiments, the patient has hypertension. In yet other related embodiments, the patient has serum fibronectin. In still other embodiments, the patient has reduced blood pressure relative to the average pressure for a healthy individual comparable in age, race, gender, and/or stage of renal disease. In still other embodiments, the patient is greater than 55 years in age. In still other embodiments, the patient is an end stage renal disease patient. In still other embodiments, the patient is in need of hemodialysis but is not an end stage renal disease patient. In still other embodiments, the patient is male. In still other embodiments, the patient is female. In still other embodiments, the patient is African American.

In certain embodiments of the methods of the invention, the patient has an average hemostasis time of about (a) 12 to 15, (b) 15 to 18, (c) 18 to 21, or (d) 21 to 24 minutes using compression alone. In certain embodiments of the methods of the invention, the patient has an average hemostasis time greater than 11 minutes using compression alone. In certain embodiments of the methods of the invention, the compression is applied with a vasoconstrictor and/or coagulant for (a) fewer than 11 minutes, (b) about 9 to 10 minutes, (c) about 8 to 9 minutes, or (d) about 7 to 8 minutes.

According to another aspect of the invention, the invention provides for a kit comprising in one or more containers a composition comprising an amount of a vasoconstrictor and/or coagulant effective for reducing or ceasing post-hemodialysis bleeding; and a pharmaceutically acceptable carrier, and instructions for practicing the methods of the invention. In certain embodiments, the instructions provide for topically applying the composition at a hemodialysis vascular access site where compression is applied for about one to fourteen minutes, resulting in a reduction in vascular access complications.

The invention yet further provides for a method for reducing bleeding from a hemodialysis vascular access site, comprising applying topically as part of a hemodialysis therapy to a hemodialysis vascular access site during a hemodialysis session a composition comprising an amount of a vasoconstrictor or coagulant effective for reducing or ceasing post-hemodialysis bleeding at the vascular access site; and applying compression to the hemodialysis vascular access site for a period sufficient to achieve cessation or reduction of blood flow out of the hemodialysis vascular access site, such that a cessation or reduction of bleeding from the hemodialysis vascular access site is achieved in about one to fourteen minutes, for the majority of hemodialysis sessions of the therapy.

3.1. Terminology

The term "reduce" (in reference to blood flow) means that blood flow from a vascular access site has decreased to a rate or amount that is acceptable such that the patient is not in need of supervision and can leave the hemodialyis facility.

The term "hemodialysis session" means the period of time beginning when hemodialysis needles are inserted into a vascular access site of a patient that will undergo hemodialysis and includes the time hemodialysis is performed and bleeding following removal of hemodialysis needles up to time hemostasis is reached and compression is no longer needed. Hemodialysis therapy comprises at least four hemodialysis sessions or is for at least one week. In certain embodiments, hemodialysis therapy is measured from the beginning of use of a newly matured vascular access site. In certain other embodiments, hemodialysis therapy is measured from the beginning of the use of the methods of the invention.

The term "vascular access site" means: the surgically created vascular connection between an artery and vein in addition to the contiguous enlarged portion of the connected blood vessels; the surgically implanted synthetic grafts connecting blood vessels; or the site of insertion or removal of hemodialysis needles.

The term "vascular access complication" means any cause that reduces blood flow through the hemodialysis vascular access site including, for example: ischaemic vascular disease, hyperplasia, intimal hyperplasia, thrombosis, hematoma, venous stenosis, arterial stenosis, or infection. Blood flow through the vascular access site, measured when the patient is at rest and no compression is being applied, is reduced in comparison to blood flow through the vascular access site, measured when the patient is at rest and no compression is being applied, at an earlier time, prior to multiple hemodialysis sessions, or when the site has matured but has not yet been used for hemodialysis.

The term "about" means±10% of the value the term to which the term is applied.

4. DETAILED DESCRIPTION OF THE INVENTION

The present invention relates to methods and kits useful for reducing vascular access complications associated with hemodialysis therapy and prolonging the period of time at vascular access site can be used in a patient. Hemostasis is typically obtained by a least 15-20 minutes of manual compression following hemodialysis. While this time is an inconvenience to the patient, the experimentation and results of the Applicants' demonstrate that such a prolonged compression time is also the cause of vascular access complications. The present invention is based in part on the inventors' determination that a reduction in the compression time to a period of about one to fourteen minutes, repeated, preferably, for the majority of hemodialysis sessions results in a reduction in, prevention, or inhibition of, vascular access complications.

Without being bound by any particular mechanism by which the methods of the invention achieve the desired goals, inventors believe that prolonged stasis of blood through the portion of the vascular access site where the artery and vein are connected or where the synthetic graft is located causes complications such as, but not limited to, clotting, stenosis, or hyperplasia. These complications result in a reduction in blood flow through the vascular access site in the absence of compression which decreases the efficiency or ability to effectively perform hemodialysis. The site where the hemodialysis needles are removed, i.e., the site where compression is typically applied, may differ from the location in the vascular access site as the A-V fistula connection or graft, since vascular access sites can be, for example, brachial cephalic or radial cephalic.

In one aspect, methods for reducing vascular access complications of the present invention comprise topical administration of compositions comprising a vasoconstrictor and/or coagulant. In another aspect, methods for reducing vascular access complications of the present invention comprise topical administration of a barrier-forming material. Presented below, is, first, a description of compositions suitable for use in conjunction with the methods of the invention and, second, a description of the methods and kits of the invention.

4.1. Compositions for Use in the Methods of the Invention

The compositions for use in the methods and kits of the invention can comprise a barrier-forming material for topical administration. Such barrier-forming materials can, for example, comprise a vasoconstrictor and/or a coagulant. In addition, the compositions for use in the methods and kits of the invention can comprise a vasoconstrictor and/or a coagulant in an amount effective for reducing or ceasing post-hemodialysis bleeding at a vascular access site. The compositions may contain other components, for example, anti-bacterial agents, anti-viral, or anti-fungal agents to prevent infection associated with hemodialysis. Various formulations of the compositions can be used in the methods and kits of the invention, including, but not limited to, solid compositions, gels, foams, or liquids that can be applied topically to a vascular access site. The compositions for use in the methods and kits of the invention reduce the compression needed to stop bleeding from a hemodialysis vascular access site. The reduction in compression, to about one to fourteen minutes, more preferably to one to eleven minutes, and more preferably to one to ten minutes, per hemodialysis session, results in a reduction in vascular access complications, relative to compression without coagulant or vasoconstrictor (e.g., compression with gauze alone).

In addition to the above, the present invention also encompasses use of the methods of Examples 1 and 2 in conjunction with compositions that will further reduce the period of time required to achieve hemostasis in the hemodialysis patient population. Such compositions may comprise, but are not limited to, one or more vasoconstrictors, coagulants, anti-inflammatory compounds, and combinations thereof, that are topically administered to the vascular access site. In particular instances, such compositions are topically applied as part of a composition comprising a barrier-forming material.

4.1.1. Vasoconstrictors

In one embodiment, the composition for use in the methods and kits of the invention may include one or more vasoconstrictors. The vasoconstrictor(s), for example, can be one or more of the following: endothelin-1, epinephrine, phenylephrine, serotonin, thromboxane, norepinephrine, prostaglandin, methergine, oxytocin, or isopreland U-46619 (Cayman Chemical, Ann Arbor, Mich.; a stable prostaglandin endoperoxide analog which serves as a thromboxane mimetic).

The vasoconstrictors may be used in standard recommended dosages, or, in certain embodiments, in dosages of no greater than approximately 30%, 50%, 70%, 80%, or 90% of the standard recommended dosage.

4.1.2. Coagulants

In one embodiment, the composition may include one or more coagulants. The coagulant(s), for example, can be one or more of the following: alpha-2-antiplasmin, alpha-1-antitrypsin, alpha-2-macroglobulin, aminohexanoic acid, aprotinin, beta$_2$-glycoprotein I, a source of calcium ions, calcium alginate, calcium-sodium alginate, casein kinase II, chitin, chitosan, collagen, cyanoacrylates, epsilon-aminocaproic acid, Factor X, Factor IX, Factor X, Factor XIII, fibrin, fibrin glue, fibrinogen, fibronectin, gelatin, living platelets, methacrylates, PAI-1, PAI-2, p-GlcNAc, plasmin activator inhibitor, plasminogen, platelet agonists, protamine sulfate, protein C, prothrombin, an RGD peptide, sphingosine, a sphingosine derivative, thrombin, thromboplastin, or tranexamic acid. In one embodiment, the composition for use in the methods and kits of the invention does not comprise a coagulant. In another embodiment, the composition does not comprise thrombin. In a related embodiment, the composition does not comprise bovine thrombin.

The coagulatns may be used in standard recommended dosages, or, in certain embodiments, in dosages of no greater than approximately 30%, 50%, 70%, 80%, or 90% of the standard recommended dosage.

4.1.3. Other Components

The compositions for use in the methods and kits of the present invention can comprise additional components. For example, the compositions may contain other components, for example, anti-bacterial agents, anti-viral, or anti-fungal agents to prevent infection associated with hemodialysis. The compositions for use in the methods and kits of the invention can also comprise wound-healing and/or pain-reducing agents. Such agents include anti-inflammatory agents, both steroidal and non-steroidal, such as, but not limited to, agents which inhibit leukocyte migration into the area of the puncture in the blood vessel or graft of the vascular access site (e.g., silver sulfadiazinem acetylsalicylic acid, indomethacin, and Nafazatrom), anti-histamines (e.g., pyrilamine, chlorpheniramine, tetraydrozoline, antazoline, cortisone, hydrocortisone, beta-methasone, dexamethasone, fluocortolone, prednisolone, triamcinolone, indomethacin, and sulindac, its salts and its corresponding sulfide); agents which inhibit free radical formation (e.g., superoxide dismutase (SOD), catalase, glutathione peroxidase, b-carotene, ascorbic acid, transferring, ferritin, ceruloplasmin, and desferrioxamine alpha-tocophenol); and bacteriostatic agents or bacteriocidal agents, (e.g., cefoxitin, n-formamidoyl thienamycin, tetracyclines, chloramphenicol, neomycin, gramicidin, bacitracin, sulfonamides, oxacillin, gentarnycin, gentamycin, mupirocin, kanamycin, vancomyacin, amikacin, sisomicin, silver, silver tobramycin, norfloxican, nitrofurazones, and the combination of flouroalanin/pentizidone).

The compositions for use in the methods and kits of the invention can also include a pharmaceutically acceptable carrier such as, but not limited to, conventional excipients, e.g., pharmaceutically acceptable organic or inorganic carrier substances suitable for topical application which do not deleteriously react with the compositions of the invention. Suitable pharmaceutically acceptable carriers include but are not limited to water, salt, sugar solutions, etc. The pharmaceutical preparations can be sterilized and if desired mixed with auxiliary agents.

In one embodiment, the composition for use in the methods and kits of the invention does not comprise an agent that has allergenic properties. Vasoconstrictors and/or coagulant agents as well as pharmaceutical carriers and other components can easily be tested for allergic activities by methods known to those of skill in the art. For example, delayed hypersensitivity skin tests are of great value in determining allergic reactions to agents in hemodialysis patients or in animal models (Sato et al., 1995, Clin. Immunol. Pathol. 74:35-43).

Erythropoietin, epoetin alfa recombinant epogen, or Epogen™, has 3,000 units of recombinant erythropoietin, 2.5 mg albumin (human) in sterile buffered solution (pH 6.9+/−0.3) of sodium citrate (5.8 mg), sodium chloride (5.8 mg), citric acid (0.06 mg), in water for injection. Uses of erythropoietin include stimulating the body to make red blood cells. Loss of blood cells due to excessive and repeated bleeding can lead to decreased hematocrit levels, anemia, and other complications (Eschbach, 2002, J. Am. Soc. Nephrol. 13:1412-1414). Hemodialysis patients can exhibit decreased hematocrit levels. The methods of the invention result in a reduction in bleeding associated with hemodialysis, a reduction in interventions due to vascular access complications, and/or a reduction in vascular access complications, which in turn reduces the need for erythropoietin. In one embodiment, the methods of the invention the patient is not concurrently treated with erythropoietin. In one embodiment, wherein erythropoietin is administered to the patient, the amount of erythropoietin is reduced in comparison to hemodialysis patients for whom compression is applied for a period of greater than about fourteen minutes for the majority of hemodialysis sessions.

4.1.4. Poly-β-1→4-N-Acetylglucosamine

Section 2 above incorporates by reference numerous U.S. patent documents that describe in detail the structure of poly-β-1→4-N-acetylglucosamine, any of which can be used in the compositions used in the methods and kits of the invention.

In preferred embodiments, poly N-acetylglucosamine is derived from the process of a) treating a microalgae comprising a cell body and a poly N-acetylglucosamine with a agent, e.g., hydroflouric acid, capable of weakening of the cell wall of a micoralga for a sufficient time so that the poly N-acetylglucosamine is released from the cell body; b) segregating the poly N-acetylglucosamine from the cell body; and c) removing all or, substantially all organic contaminants, and substantially all inorganic contaminants from the segregated poly N-acetylglucosamine, so that the poly N-acetylglucosamine species is isolated. The poly N-acetylglucosamine used in the methods of the invention is preferably biocompatible and/or immunoneutral.

As used herein derivatives of a poly N-acetylglucosamine polymer include: a semi crystalline form of a poly N-acetylglucosamine polymer; a poly N-acetylglucosamine polymer comprising about 50 to about 150,000 N acetylglucosamine monosaccharides covalently attached in a β-1→4 conformation, and said polymer has a molecular weight of about 10,000 daltons to about 30 million daltons; a poly β-1→4-acetylglucosamine polymer comprising about 50 to about 50,000 N acetylglucosamine monosaccharides covalently attached in a β-1→4 conformation, and said polymer has a molecular weight of about 10,000 daltons to about 10 million daltons; a poly β-1→4-acetylglucosamine polymer comprises about 50 to about 10,000 N acetylglucosamine monosaccharides covalently attached in a β-1→4 conformation, and said polymer has a molecular weight of about 10,000 daltons to about 2 million daltons; a poly β-1→4-acetylglucosamine polymer comprising about 50 to about 4,000 N acetylglucosamine monosaccharides covalently attached in a β-1→4 conformation, and said polymer has a molecular weight of about 10,000 daltons to about 800,000 daltons; and a semi crystalline poly β-1→4-N acetylglucosamine polymer comprising at least one N acetylglucosamine monosaccharide that is deacetylated, and wherein at least 40% of said N acetylglucosamine monosaccharides are acetylated. Derivatives of a poly β-1→4-N-acetylglucosamine polymer also include compositions that are about 100%, 90%, 80%, 70%, 60%, 50%, 40%, 30%, 20%, 10% or less poly β-1→4-N-acetylglucosamine. The poly-p-1→4-N-acetylglucosamine polymer can be purified. The poly-α-1→4-N-acetylglucosamine polymer can be acetylated. The poly-β-1→4-N-acetylglucosamine polymer can be deacetylated. The poly-β-1→4-N-acetylglucosamine polymer can be free of protein, substantially free of other organic contaminants, and substantially free of inorganic contaminants. The poly-β-1→4-N-acetylglucosamine polymer can be semi-crystalline. The poly-β-1→4-N-acetylglucosamine polymer can be biodegradable and biocompatible. The poly-β-1→4-N-acetylglucosamine polymer can have a molecular weight of about 800,000 daltons to about 30 million daltons. The poly-β-1→4-N-acetylglucosamine can comprise semi crystalline having a molecular weight of about 800,000 daltons to about 30 million daltons. The poly-β-1→4-N-acetylglucosamine polymer can have a molecular weight of about 10,000 daltons to about 800,000 daltons. The poly-β-1→4-N-acetylglucosamine can comprise semi crystalline having a molecular weight of about 10,000 daltons to about 800,000 daltons. In one embodiment, the methods and kits of the invention have the proviso that the composition does not comprise poly-β-1→4-N-acetylglucosamine or a derivative thereof.

4.1.5. Formulations of the Compositions of the Invention

The composition for use in the methods and kits of the invention can be formulated in any number of ways, including, but not limited to, a gel, solid, liquid, sponge, foam, spray, emulsion, suspension, solution, string, microbead, microsphere, or microfibril. The compositions can include, for example, a pharmaceutically acceptable carrier, a neutral liquid, neutral gel or neutral solid. In certain preferred embodiments, the composition is formulated as a barrier, membrane, or film. Moreover, the composition can be added to a barrier, membrane, or film, such as a backing. A barrier, membrane, or film can be supplied in a variety of standard sizes, which can be further cut or sized to the area being treated. The barrier, membrane, or film can be, for example, a conventional bandage or gauze to which the composition of the invention is added or coated on, prior to application to the patient. In another embodiment, the composition can be administered topically followed by application of a barrier, membrane, or film. Alternatively, the composition can be, for example, formulated as a barrier, membrane, or film made out of, for example, strings, microbeads, microspheres, or microfibrils, or the composition can be formulated as a barrier-forming mat.

In certain embodiments, the composition is formulated as a gel. The gel can be of varying viscosity. For embodiments where the gel is applied to a bandage to topically treat a site of needle puncture, a low viscosity is desired. For gels, higher viscosity may be desired if the composition is intended to remain in a location rather than dissipate rapidly. Viscosity is the quantity that describes a fluid's resistance to flow, while the range of viscosity is a continuum. For example, as a frame of reference, not as a limitation of the meaning of viscosity, the viscosity values of about 1-4 centipoise (cP) generally are typified by fluid compositions. Viscosity values of about 5-14 cP generally are typified by gel-like compositions, while viscosity values of 15-20 cP are relatively hard compositions such as plastics. The viscosity of cell cytoplasm is about 11 cP. In certain embodiments, the viscosity of the compositions for topical administration in the methods and kits of the invention is about 10 cP. Viscosity can be measured with, for example, a Saybolt International B. V. (Vlaardingen, The Netherlands). One skilled in the art can also routinely use other measurement techniques and devices common in the art.

In certain embodiments of the invention, the composition is formulated as a membrane. In other embodiments, the composition is in a container within or coated on a membrane. The membranes may be porous or relatively continuous. In preferred embodiments the membranes are made of woven polymer fibers. Such membranes are particularly useful in treatment of wounds on the skin surface.

In one embodiment, the composition for use in the methods and kits of the invention comprises, barrier-forming materials, for example, a patch made of barrier-forming materials. In another embodiment, the composition comprises a material, e.g., a barrier-forming material, coated with a composition of the invention. In one such embodiment, the composition comprises a gauze coated with a composition of the invention. In certain embodiments, the composition comprises a barrier-forming material coated with the composition of the invention, wherein the barrier-forming material also contains an adhesive so that the material can adhere to a patient's skin surface. Alternatively, the composition can lack barrier-forming materials.

In another embodiment, where the composition for use in the methods and kits of the invention encompasses an adhesive barrier-forming material, the composition can be topically adhered to cover a skin surface wound caused by removal of hemodialysis needles that is contiguous with a vascular access site without applying pressure to compress the vascular access site.

The compositions for use in the methods and kits of the invention can include a backing. For example, if the composition is formulated as a patch, a backing can be adhered to the patch. The backing can, for example, be coated or embedded with any adhesive compound so that areas of the backing that contact the skin will adhere the backing and the attached composition of the invention to the skin surface of the patient. The type of adhesive used can be any type of medically acceptable adhesive. Such backings can be made of natural polymers or synthetic materials. Natural polymers from which the backing can be made include, but are not limited to, cellulose and xylan. Synthetic materials from which the backing can be made include, but are not limited to, polyurethane, Teflon, Dacron, stainless steel mesh screen, and a polyester woven fabric. Preferably the backing and adhesive are porous to areas which contact the skin to allow diffusion of oxygen. The backing can also serve as a surface upon which manual compression can be applied.

4.2. Methods for Reducing Vascular Access Complications

In general, the invention relates to methods for reducing vascular access complications associated with a hemodialysis therapy in a patient comprising applying topically to a hemodialysis vascular access site during a hemodialysis session a composition comprising an amount of a vasoconstrictor or coagulant effective for reducing or ceasing post-hemodialysis bleeding at the vascular access site, and applying compression to the hemodialysis vascular access site for a period of about one to fourteen minutes, so that compression is applied to the hemodialysis vascular access site for a period of about one to about fourteen minutes, for repeated hemodialysis sessions, preferably for the majority of hemodialysis sessions of the therapy and the number of vascular access complications associated with the hemodialysis therapy is reduced in comparison to hemodialysis patients for whom compression is applied for a period of greater than about fourteen minutes for the majority of hemodialysis sessions.

In certain embodiments of the methods of the invention, the method steps are repeated at least about 4, 5, 6, 7, 8, 9, or 10 times. In certain embodiments of the methods of the invention, the methods include the step of repeating the first two steps of applying composition and compression at least about 4, 5, 6, 7, 8, 9, or 10 times. In certain embodiments, the methods of the invention are practiced for at least about 50% of the hemodialysis sessions of a hemodialysis therapy regimen. In certain embodiments, the methods of the invention are practiced for at least about 70% of the hemodialysis sessions of a hemodialysis therapy regimen. The regimen is preferably at least one week, at least one month, at least two months, at least three months, or at least six months in duration, with anywhere from 0, 1, 2, 3, or more hemodialysis sessions per week. In other embodiments, the methods of the invention are practiced during at least 50% of the hemodialysis sessions over a six month period.

In certain embodiments, the hemodialysis regimens of the invention are greater than one week in duration, wherein a patient typically receives 1-3 hemodialysis sessions. For example, the hemodialysis regimens of the invention may comprise at least 4, 5, 6, 7, 8, 9, or 10 hemodialysis sessions. In certain embodiments, the hemodialysis regimens of the invention are at least ten months in duration. In yet other embodiments, the hemodialysis regimens of the invention are at least about 1, 2, 3, 4, 5, 6, 7, 8, 9, 10, 11, 12, 13, 14, 15, 16, 17, 18, 19, 20, 25, or 30 years in duration. In a preferred embodiment, the hemodialysis regimens of the invention is at least 5-15 years in duration. The methods described herein are preferably practiced during at least 10%, 20%, 30%, 40%, 50%, 60%, 70%, 80%, 90%, or 100% of hemodialysis sessions. The hemodialysis sessions of the invention are useful for prolonging the use of vascular access sites. Thus, the use of a particular vascular access site can be maintained or prolonged for at least about 1, 2, 3, 4, 5, 6, 7, 8, 9, 10, 11, 12, 13, 14, 15, 16, 17, 18, 19, 20, 25, or 30 years as a result of practicing the methods described herein. In certain embodiments, the number of times a particular vascular access site is used is decreased in comparison to hemodialysis practiced without the methods of the invention, for example using compression with gauze alone. In other embodiments, the number of hemodialysis sessions needed by the patient is decreased in comparison to hemodialysis practiced without the methods of the invention, e.g., using compression with gauze alone.

In certain embodiments of the methods and kits of the invention, the vascular access complication is hyperplasia, thrombosis, hematoma, venous stenosis, arterial stenosis, infection, or morbidity. In certain embodiments, the methods and kits of the invention are useful for treating complications arising from long-term hemodialysis regimens, for example, hyperplasia, thrombosis, venous stenosis, arterial stenosis, or morbidity. Such long-term complications typically develop as a results of multiple hemodialysis sessions, for example about 4, 6, 8, 10, 15, 20, 25, 30, 35, 40 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, or 365 sessions. Hematoma or infection typically arise from the practice of hemodialysis in the short-term, for example, from a 1 day, 2 days, 3 days, 4 days, 5 days, 6 days, 1 week, 2 weeks, 3 weeks, 1 month, 2 months, or 3 months of hemodialysis sessions.

In certain embodiments, the methods of the invention are utilized for about one year, the percent morbidity is about 19%, 18%, 17%, 16%, 15%, 14%, 13%, 12%, 11%, 10%, 9% or 8% in comparison to compression alone without the application of a coagulant or vasoconstrictor. In certain embodiments, the methods of the invention are utilized for about one year, the 5 year survival rate is increased to about 30%, 32%, 35%, 40% or greater in comparison to use of gauze alone. Utilizing the methods of the invention to reduce compression time, life is extended for about 1 month, 2 months, 3 months, 4 months, 5 months, 6 months, 7 months, 8 months, 9 months, 10 months, 11 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, or 10 years.

In certain embodiments, where the patient has a mature A-V fistula or A-V graft vascular access complications are reduced as a result of using the methods and kits of the invention and in comparison to the percent of complications that arise without the kits and methods of the invention.

The percent of complications can be measured using imaging techniques described herein or compared to the known intervention rates or length of time until vascular access complications require a first intervention, where intervention is needed due to vascular access complications (Schwab, 1999, Kidney International, 55:2078-2090). In addition to reducing the number of vascular access complications, the methods of the invention reduce the severity of vascular access complications. For example, the severity of stenosis may be determined by the rate or amount of blood flow through the vascular access site or the severity of thrombosis may be determined by measuring the frequency and/or the dimensions of blood clots. Severity of hematomas may be determined by measuring the frequency and/or the dimensions of hematomas or the duration of a hematoma. In certain embodiments of the methods of the invention, the risk of short-term and/or long-term complications is reduced. In certain embodiments of the methods of the invention, reducing the risk means reducing the severity or number of short-term and/or long-term vascular access complications by about 5%, 10%, 20%, 30%, 40%, 50%, 60%, 70%, 80%, 90%, or more. In certain embodiments, the reduced risk is in comparison to the same patient where the methods and kits of the invention are not used (e.g., using compression alone with gauze). In certain embodiments, the reduced risk is in comparison to the a patient population where the methods and kits of the invention are not used (e.g., using compression alone with gauze).

The compositions applied contribute to achieving a reduction or cessation of blood flow from the hemodialysis vascular access site, in particular, the site of removal of hemodialysis needles, relative to compression alone such that compression time can be shortened. This reduction in compression time in turn results in a reduction in vascular access complications associated with hemodialysis therapy, the average number of vascular access sessions associated with a hemodialysis therapy, the infection rate associated with hemodialysis therapy, or a preservation of access to a hemodialysis vascular access site.

Generally, the methods of the invention, are intended for patients that do not normally, (e.g., over repeated hemodialysis sessions) exhibit a cessation or reduction of blood flow out of, e.g., bleeding from, of the hemodialysis vascular access site in less than about one to about fourteen minutes, with compression in the absence of a composition of the invention. The methods and kits of the invention would provide the greatest benefits for this class of patient. Some patients in the hemodialysis population have hemostasis times naturally fewer than about 14 minutes. In certain embodiments, the methods of the invention are not utilized for patients who exhibit rapid hemostasis times using compression and gauze alone, for example hemostasis times of 9, 8, 7, 6, 5 minutes or less.

4.2.1. Administration of Anticoagulants

In certain embodiments of the invention, the methods and kits of the invention may be administered to a patient to whom an anticoagulant in an effective amount to prevent coagulation of blood has been administered. Examples of anticoagulants that may be used in conjunction with the invention include, coumadin™, dicumarol™, warfarin™, ecotrin™, heparin, nadroparin, aspirin, an antiplatelet drug, or a thrombolytic agent. Typically, full dose of heparinization for more than 12 hours before a medical procedure is common. In other protocols heparin is administered at repeated intervals to ensure that a constant active clotting time is maintained (Falstrom et al., 1997, Catheterization and Cardiovasular Diagnosis 41:79-84). In one embodiment, the anticoagulant can be administered separately from the compositions of the invention, either concurrently or prior to administration of the compositions. For those patients to whom an anticoagulant has been administered prior to hemodialysis, the composition of the invention may further comprise one or more agents that locally neutralize the effect of the administered anticoagulant. In patients to whom heparin has been administered the composition may further comprise protamine sulfate in an amount effective to locally neutralize heparin.

In certain embodiments of the invention, protamine sulfate in an effective amount to locally neutralize heparin at the vascular access site is administered. In one embodiment, protamine sulfate can be administered separately from the compositions of the invention, either concurrently or prior to administration of the compositions.

4.2.2. Administration of Compositions Comprising a Vasoconstrictor

Following removal of the dialysis needles, a formulation comprising an effective amount of a selected vasoconstrictor compound can be applied to each needle site. The formulation can be directly applied to a vascular access site as an adherent composition or may be embedded within or coated upon another material that is held in place with an adhesive material. If necessary or desired, the formulation, composition, or material containing the composition is held in place with firm digital pressure for a period of time that is less than about 14 minutes, preferably, less than about 10 minutes, after which bleeding is arrested. In certain embodiments, the period of time is less than about 5 minutes.

For example, in the Examples presented herein below, the composition will adhere to the patient's skin at the vascular access site, or, can be used to coat another material that is applied to the patient's skin. For example, the Examples presented herein below, the composition can be coated onto a barrier membrane to which is attached an oxygen-permeable Teflon backing. The backing extends beyond the edges of the barrier membrane and comprises an adhesive material suitable for holding the barrier membrane to the patient's skin, thereby forming an adhesive patch. For example, in the Examples presented herein below, the barrier membrane is a barrier-forming mat constructed with poly-β-1→4-N-acetylglucosamine polymers and coated with a gel comprising of the vasoconstrictor, endothelin-1. Following removal of the dialysis needles, the Teflon-backed patch comprising endothelin-1-coated onto the poly-β-1→4-N-acetylglucosamine-containing, barrier-forming mat is adhered to the vascular access sites. In the Examples presented herein below, for example, digital pressure is not applied to the patch, which remains attached to the patient's skin until removed by the patient at his/her convenience. However, in the Examples presented below, if digital pressure is applied, it is applied for a period of less than ten minutes, preferably less than about 5 minutes.

4.2.3. Administration of Compositions Comprising a Coagulant

Following removal of the dialysis needles, a formulation comprising an effective amount of a selected coagulant can be applied to each needle site. The formulation can be directly applied to a vascular access site as an adherent composition or may be embedded within or coated upon another material that is held in place with an adhesive material. If necessary or desired, the formulation, composition, or material containing the composition is held in place with firm digital pressure for a period of time that is less than about 14 minutes, preferably, less than about 5 minutes, after which bleeding is arrested.

For example in the methods described in the Examples presented herein below, the composition can be formulated such that it will adhere to the patient's skin at the vascular access site, or, can be used to coat another material that is applied to the patient's skin. In the Examples presented herein below, for example, the composition is coated onto a barrier membrane to which is attached an oxygen-permeable Teflon backing. The backing extends beyond the edges of the barrier membrane and comprises an adhesive material suitable for holding the barrier membrane to the patient's skin, thereby forming an adhesive patch. In the Examples presented herein below, for example, the barrier membrane is a barrier-forming mat constructed with poly-β-1→4-N-acetylglucosamine polymers and coated with a gel comprising of the coagulant, tranexamic acid. Following removal of the dialysis needles, the Teflon-backed patch comprising tranexamic acid-coated onto the poly-β-1→4-N-acetylglucosamine-containing, barrier-forming mat can be adhered to the vascular access sites. For example, in the Examples presented herein below, digital pressure is not applied to the patch, which remains attached to the patient's skin until removed by the patient at his/her convenience. However, if digital pressure is applied, it is applied for a period of less than ten minutes, preferably less than about 5 minutes.

4.2.4. Applying Compression

Compression can be applied to the vascular access site in several ways. The present methods can entail a combination of applying pressure and contacting a barrier-forming material and/or a composition comprising a vasoconstrictor and/or coagulant agent to a site on the patient's skin surface where hemodialysis needles have been removed that is contiguous with the vascular access site. Typically, the site of application is the wound where the hemodialysis needles have been removed.

In certain embodiments of the invention, the compression is manual compression. Manual compression can, for example, be applied by pressing with the tips of fingers on the skin surface, at a point above an underlying vascular access site, so that the vascular access site is compressed and blood flow is significantly reduced or stopped in the targeted vascular access site. This type of compression can be applied at a site proximal of removal of hemodialysis needles in a vascular access site. Typically, a proximal site is between about 1 and about 10 cm proximal of the removal site. In certain embodiments of the invention, manual compression is applied directly to the site where the composition has been applied to the vascular access site. Typically the composition is applied topically to the portion of the vascular access site that is bleeding. The technique of manually pressing on a patient's skin at the correct place to reduce blood flow and blood pressure is common in the art of and is effective in both humans and other mammals (Camenzind et al., 1994, Journal of the American College of Cardiology. 24(3):655-662; Kipshidze et al., 1998, Journal of Invasive Cardiology. 10(3):133-141; Merino et al., 1992, Catheterization and Cardiovasular Diagnosis 26:319-322; Sanborn et al., 1993, Journal of the American College of Cardiology. 22(5):1273-1279).

The manual compression can be applied in combination with application of a composition comprising a vasoconstrictor and/or coagulant. Such embodiments can entail manually applying compression to a vascular access site concurrently with applying a composition as described herein above. Alternatively, manual compression can be applied immediately prior to application of a composition or immediately after application of a composition.

In an embodiment of the invention that encompasses a manual compression technique as a part of a method of the invention, the technique may be one wherein pressure is applied with one's fingers or the palm of one's hand directly over a vascular access site. In certain embodiments, compression can be applied directly to the wound site at the same angle at which the needle was inserted. In one embodiment of the invention, manual compression may be applied concurrently with application of the composition. If the composition of the invention is formulated as a barrier-forming material, then the composition and the compression can be applied at the same time. If the composition is, for example, a gel, the gel can be applied to the hemodialysis needle removal site followed immediately by compression, or the gel might be applied to a barrier-forming material such as gauze and the treated gauze can then be applied at the same time as compression.

In applying manual compression techniques, the amount of pressure applied and the consistency of pressure force generally varies over time and among individuals applying the pressure. This is satisfactory as long as post-hemodialysis bleeding is reduced or ceases in about one to fourteen minutes, such that compression can be removed in about one to about fourteen minutes.

In certain embodiments, it may be preferable to apply compression to a vascular access site mechanically rather than manually. Several devices well known to those of skill in the art have been developed and are commonly used to apply compression, including C-clamps of varying or adjustable force, and compression bandages/dressings coupled with attachment of desired weights. Such compression devices may be used in conjunction with the methods of the invention and can provide a constant application of the desired compression force. In a preferred embodiment, the amount of compression force applied to the vascular access site allows for blood flow through the vascular access site. In a related embodiment, the blood flow is about 50, 10, 200, 300, 400, or 500 ml/min. In a related embodiment, the blood flow is about 5%, 10%, 15%, 20%, 25%, 30%, 35%, 40%, 45%, 50%, 55%, 60%, 65%, 70%, 75%, 80%, 85%, 90%, or 95% of the normal physiological flow rate through the vascular access site.

If non-manual compression is employed in the methods of the invention, then a constant pressure may be applied. A technique of using stepwise reduction in compression can be employed when using for example a C-clamp or compression bandage/dressing, wherein the pressure may be lessened in increments over time as necessary. A fluid-filled balloon connected to a pressure transducer can also be used to measure the amount of pressure applied.

In certain embodiments, compression is either applied first at a site proximal to the vascular access site to decrease blood flow in the vascular access site or is applied first to both the proximal site and the vascular access site simultaneously; in either case the compression applied at the proximal site is later released or decreased while the compression at the vascular access site is maintained. The time between the application of compression and the release of pressure at the proximal site can be about 15 seconds, 30 seconds, 1 minute, 1.5 minutes, 2 minutes, 2.5 minutes, 3 minutes, 3.5 minutes, 4 minutes, 4.5 minutes, or 5 minutes. In other embodiments, compression is applied and maintained at both the proximal and vascular access sites.

The amount of compression force varies for each patient and vascular access site being treated. Any of the compression techniques described herein can be used in carrying out the methods of the invention, as well as other standard compression techniques. Various methods for measuring compression time and compression force can be employed in carrying out the methods of the invention as described above.

4.2.5. Compression Time

One of the advantages of the methods of the present invention is that the combination of compression and the compositions results in a reduction in compression time needed to reduce or cease the flow of blood from the vascular access site which leads to a reduction in vascular access complications relative to patients who receive longer periods of compression. The amount of time for which compression is maintained to achieve hemostasis, i.e., a cessation or reduction of blood flow from a skin surface wound contiguous with a vascular access site, is subject to the size of the wound and the period of time for which pressure is applied in compressing the blood vessel. As used herein in connection with the invention, hemostasis means cessation or reduction of blood flow from a skin surface wound contiguous with a vascular access site. The amount of time for which compression is maintained when carrying out the methods of the invention is shorter for the majority of hemodialysis sessions in comparison to compression alone or compression without a composition as measured under comparable circumstances.

In one embodiment of the invention, the compression time necessary to cease or reduce bleeding is less time than necessary when applying compression in conjunction with a topical barrier-forming material without a vasoconstrictor and/or coagulant. In another embodiment, the compression time is about one to fourteen minutes, for the majority of hemodialysis sessions in comparison to applying compression in conjunction with a topical barrier-forming material without a vasoconstrictor and/or coagulant, and vascular access complication occurrence decreases.

In certain instances, the period of time for which compression is applied may be fewer than about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, or 14 minutes. In certain embodiments, the period of time for which compression is applied is greater than 11 minutes. In certain embodiments, the period of time for which compression is applied is about 11 to 25 minutes. In one embodiment, compression is applied for a period of about one to fourteen minutes, for the majority of hemodialysis sessions. The period of time begins after the hemodialysis needles are removed at the time compression is initially applied. The period of time is continuous until compression is released for the final time during the session. The period of time can include intervals of time during which compression is released momentarily to check for bleeding from the wound. In one embodiment, the period of time can include only the periods of time during which compression is applied, excluding the breaks to observe or measure bleeding.

In certain embodiments of the methods and kits of the invention where the composition comprises a vasoconstrictor and/or a coagulant, the compression time is reduced by about 2%, 5%, 8%, 10%, 15%, 20%, 25%, 30%, 35%, 40%, 45%, 50%, 55%, 60%, 65%, 70%, 75%, or 80% in comparison to compression in conjunction with a barrier-forming material having no vasoconstrictor and/or coagulant.

The time for applying compression, manual or otherwise, in conjunction with a composition of the invention may be divided into intervals between which there is a release or partial release of compression, for example, in order to record observations to calculate the cessation rate or time of blood from a wound and/or to calculate the time to achieve hemostasis. The compression intervals may, for example, be about 5, 10, 15, 20, 25, 30, 35, 40, 45, 50, 55, or 60 seconds in length. Alternatively, the time intervals may be 1, 1.5, 2, 2.5, 3, 3.5, 4, 4.5, 5, 5.5, 6, 6.5, 7, 7.5, 8, 8.5, 9, 9.5, or 10 minutes in length. In a preferred embodiment, the bleeding is checked once about halfway through the desired time of compression. In a related embodiment, the bleeding is checked after about 5 minutes of compression. Generally, the periods between compression intervals are about 1-10 seconds in length.

In another embodiment, compression is applied for time intervals of equivalent length. The total compression time continuous or interrupted to determine bleeding time is about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, or 14.5 minutes. In one embodiment, compression is applied to the desired vascular access site immediately following the removal of the hemodialysis needles.

The compositions described in section 4.1. are preferably applied concurrently with an initial application of compression in the methods of the invention. In other embodiments, the compositions can be re-applied at compression intervals. In other embodiments, compression is applied for a time period prior to application of a composition and further compression. In one embodiment, the time period prior to application of a composition is about 1, 2, 3, 4, or 5 minutes.

4.2.6. Measurement of Time or Rate of Blood Flow or Cessation of Bleeding

In certain embodiments, the rate or time of cessation or reduction is measured to determine if cessation or reduction of blood flow (e.g., bleeding) out of a hemodialysis needle wound is achieved in about one to about fourteen minutes. The rate or time of cessation or reduction in the presence or absence of a composition can also be measured for comparison purposes.

Additional techniques that can be used with the methods of the invention described herein to observe cessation or reduction of blood flow out of the vascular access site or rate of blood flow through the vascular access site are taught below 4.2.5.

The rate of or time to achieve cessation or reduction of blood flow out of the vascular access site can be calculated simply as the total number of time intervals required to achieve the effect, provided the time intervals are equivalent for each treatment, i.e. compression alone or compression in conjunction with the composition of the invention. For example if the sum of the number of time intervals required for all patients receiving a first treatment is 8 and if the sum of number of time intervals required for all patients receiving a second treatment is 10, then the percent difference would be 25%. Alternatively, the average time to achieve cessation or compression time could be calculated for each treatment group, then compared to determine the percent difference.

In another embodiment, the time to achieve cessation of compression time is measured in minutes and/or seconds rather than time intervals. The percent difference between the times measured can be calculated with one of the methods described above for the time intervals method.

In certain embodiments of the invention, the hemodialysis patient has a mean hemostasis time of about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes. In certain embodiments, the patient has a mean hemostasis time greater than 11 minutes.

Where the time to achieve cessation or reduction of blood flow from the vascular access site caused by removal of hemodialysis needles from a vascular access site is measured in minutes and/or seconds, the number of time intervals for which compression is applied may not necessarily be a factor in calculating the time to cessation. Total time from application of treatment to cessation or reduction of blood flow can be compared for the two treatment groups. In this embodiment of the invention, compression alone may be initially applied for a longer period of time than compression in conjunction with a composition as described herein above in section 4.2.5. since values for the time to achieve cessation are known in the art for compression alone. The time to achieve cessation or the rate of cessation of blood flow can also be measured for the circumstance where only compression is applied. The above described measurements can be made by imaging methods known to one of skill in the art, including but not limited to ultrasonography and scintigraphic imaging. For example, compression alone may be applied to a patient for five minutes before an observation is recorded, while the patient receiving compression in conjunction with the composition of the invention would require compression to be partially and briefly released to make blood flow observations, in order to obtain data to calculate the time to achieve cessation or total compression time for a hemodialysis session.

If a set number of compression time intervals is applied, the percent difference can be calculated based on the number of patients in each treatment group. For example, if compression is applied for two time intervals and 60 of 100 patients receiving a first treatment consisting of compression alone achieve cessation of bleeding after two compression intervals, and 80 of 100 patients receiving a second treatment consisting of compression plus the composition of the invention achieve cessation or sealing of a wound after two equivalent time intervals, then the percent difference in time to achieve hemostasis or the total compression time for a hemodialysis session would be 20%.

The frequency of thrombosis occurrence or other vascular assess complications can be calculated with clinical observations. One indicator of thrombosis is reduction of blood flow through the vascular access site. The reduction of blood flow through the vascular access site can be in comparison to the flow rate before the hemodialysis session started or physiological standard flow rate which could be readily determined from standard references. Alternatively, diagnoses of stenosis or other vascular complications as well as compression time to achieve cessation of blood flow and amount of sealing of the wound may also be made with various imaging techniques.

The reduction in vascular access complications can be measured or quantified in several ways. For example, comparisons can be made among groups of patients, where one group serves as a control and receives standard hemodialysis therapy and another group receives hemodialysis therapy with the methods of the invention. The mean numbers of vascular access complications can then be compared for the groups to identify reductions in the occurrence of vascular assess complications. The reduction in vascular access complications can also be measured within a patient by comparing the numbers of vascular access complications during periods of hemodialysis sessions with and without the methods of the invention. Standard medical statistical methods can be used to identify reductions, such as those methods described below.

In various embodiments, vascular access complications decrease by about 5%, 10%, 20%, 30%, 40, 50%, 60%, 70%, 80%, 90% or 100% for a patient or patient population administered the methods of the invention.

In one aspect of the invention, the rate of cessation or reduction of blood flow when employing the methods of the invention is 10% greater than applying compression in conjunction with a topical barrier or gauze without a vasoconstrictor and/or coagulant. In other aspects, the rate as described above is 10%, 15%, 20%, 25%, 30%, 35%, 40%, 45%, 50%, 60%, 70%, 80% or greater.

In one aspect of the invention, the time to achieve cessation or reduction of blood flow when employing the methods and compositions of the invention is 10% less than applying compression in conjunction with a topical barrier or gauze without a vasoconstrictor and/or coagulant. In other aspects, the time as described above is 10%, 15%, 20%, 25%, 30%, 35%, 40%, 45%, 50%, 60%, 70%, 80% or less relative to applying compression alone (e.g., gauze alone).

Statistical methodology can be employed to determine if the observed differences are statistically significant. In particular, the differences observed between the compression time or occurrence of vascular complications using the methods of the invention in comparison to compression alone or compression with vasoconstrictors and/or coagulants can be analyzed with standard statistical methodology. Statistical significance can be determined with any standard calculated statistic (e.g., a one-tailed t statistic, a two-tailed t statistic, a chi square statistic, an F statistic, etc.). Standard statistical methodologies suitable for use in connection with the invention include methodologies commonly used in medical analyses and clinical trials. Examples of methodologies can be found in reference publications including, but not limited to: Vogt W., 1998, Dictionary of Statistics and Methodology 2nd ed., SAGE Publications; Spiegel, D., J. Myles, and K. R., 2002, Abrams Bayesian Approaches to Clinical Trials and Health Care: Statistics in Practice. Wiley, John & Sons, Incorporated; Cleophas, T. J., A. H. Zwinderman, and T. F. Cleophas, 2002, Statistics Applied to Clinical Trials 2nd ed., Gehan, E. A. A. and N. A. Lemak, 1994, Kluwer Academic Publishers; and Statistics in Medical Research: Developments in Clinical Trials 1st ed., Kluwer Academic Publishers.

For example, color flow duplex sonography of a vascular access site can be used to test for pseudoaneurysms (Gwechenberger et al., 1997, Angiology. 48(2): 121-126.) Scintigraphic Image Analysis can be employed to examine blood flow and/or clott formation at the site of removal of hemodialysis needles or the site of A-V connection or graft and to determine if a wound in a vascular access site caused by a hemodialysis needle is effectively sealed (Ismail et al., 1995, Catheterization and Cardiovasular Diagnosis 34(1):88-95). Angiogram technology can also be used to examine sealing of a wound site caused by hemodialysis needles (Hoekstra et al., 1998, Biomaterials. 19:1467-1471). hyperplasia can be monitored and diagnosed as a vascular access complication using, for example, intravascular ultrasound (Schwab, 1999, Kidney International, 55:2078-2090). With imaging analyses as described herein, the time rate and percent difference in rates or times of cessation or reduction of blood flow from the hemodialysis needle wound or blood flow through the A-V fistulae or graft can be calculated without releasing compression to make observations. The number of vascular access complications, e.g. thrombosis events, can also be calculated with the imaging techniques described herein or with other imaging techniques well known to those of skill in the art of diagnosis vascular access complications.

In one embodiment, the methods of the invention comprise the step of measuring or monitoring the presence or development of vascular access complications or blood flow through the vascular access site. This can be achieved using, for example, the imaging techniques described below. Such monitoring may be done at each hemodialysis session or at fixed periods of time, such as every 3 months. Alternatively, the monitoring can be done if the patient exhibits a history of symptoms of vascular access complications or clinical manifestation of vascular access complications.

The blood flow rate measured can be during compression, prior to compression, subsequent to compression, or blood flow rate thought the hemodialysis machine. In certain embodiments, the blood flow through the vascular access site is measured in comparison to blood flow through the site prior to compression, at maturity of the site prior to repeated use, or physiological flow rate through the site. Schwab et al. (1989, Kidney International, 36:707-711) proposed detection of venous anastomosis, an indicator of access site thrombosis, where detection was achieved by monitoring the venous pressure at a set blood flow rate of 200 mumin during the dialysis procedure. Other techniques for monitoring or measuring blood flow through a vascular access site include recirculation (i.e., when blood pump flow demand from hemodialysis machine exceeds access blood flow as a result of late venous outlet stenosis), acute drop in dose of dialysis, access blood flow (i.e., the lower the blood flow velocity, the higher the risk of thrombosis: blood flows of $\geq$800 m/min have a higher rate of thrombosis than blood flows of $\geq$1,000 ml/min in PTFE grafts and in A-V fistulae vascular access complication risk rises if blood flow is less than about 400 mumin, or in either type of access a decrease in blood flow of 25% is indicative of vascular access complication risk), and ultrasound dilution, angiography, Intravenous digital subtraction angiography (DSA), Doppler Ultrasound, or duplex doppler color flow for measuring blood flow velocity and observing anatomical pathology.

In embodiments of the invention, where blood flow through the vascular access site is measured to determine the reduction in vascular access complications or to extend the time a vascular access site can be used for hemodialysis, blood flow is greater than about 600 m/min, 650 m/min, 700 ml/min, 750 ml/min, 800 m/min, 850 ml/min, 900 ml/min, 950 ml/min, or 1000 ml/min in the vascular access site when the methods and kits of the invention are employed and blood flow is measured prior to or following a hemodialysis session. In related embodiments, the blood flow rate in the vascular access site is less than 1500 ml/mmin.

In a preferred embodiment, the methods of the invention effectively reduce the likelihood of vascular access complications, including thrombosis.

In certain embodiments of the methods and kits of the invention where the composition comprises a vasoconstrictor and/or a coagulant, the number, rate, or percent of patients with vascular access complications is reduced by about 2%, 5%, 8%, 10%, 15%, 20%, 25%, 30%, 35%, 40%, 45%, 50%, 55%, 60%, 65%, 70%, 75%, 80%, 85%, 90%, 95% or more in comparison to compression in conjunction with a barrier-forming material having no vasoconstrictor and/or coagulant, where compression is applied for about the same period of time.

In certain embodiments of the methods and kits of the invention where the composition comprises a barrier-forming material not having a vasoconstrictor and/or a coagulant, the number, rate, or percent of vascular access complications is reduced by about 2%, 5%, 8%, 10%, 15%, 20%, 25%, 30%, 35%, 40%, 45%, 50%, 55%, 60%, 65%, 70%, 75%, 80%, 85%, 90%, 95% or more in comparison to compression for the clinical standard time, e.g., 15-20 minutes, in conjunction with a barrier-forming material, e.g., gauze, having no vasoconstrictor and/or coagulant.

4.2.6.1. Scintigraphic Image Analysis

Scintigraphic Image Analysis can be employed to examine blood flow and/or clot formation at site of removal of hemodialysis needles or a vascular access site and to determine if a wound is effectively sealed, especially in animal model systems (Ismail et al., 1995, Catheterization and Cardiovasular Diagnosis 34(1):88-95). For example, if the invention is being tested in an animal model, a camera fitted with a low energy all-purpose collimator can be placed in position over a hemodialysis vascular access site. Point sources (~50 uCi 99 mTc) in suitable containers may be used to record the exact position of the animal body, for alignment of subsequent images. The test animals are injected through with autologous technetium-labeled red blood cells, (mean=16.65±3.51 mCi), for which the labeling efficiency is previously tested. The labeled cells are allowed to circulate for 5 minutes before images are taken. Images can be taken at regular time intervals up to 24 hours. Early images can be used to ascertain sealing of a hemodialysis wound and cessation or amount of blood flow, whereas later images can be used to identify clots with great efficiency.

4.2.6.2. Angiography

An angiogram is a test in which a dye, or contrast, is administered to a patient and X-ray imaging is used to look inside blood vessels in order to diagnose or treat lesions involving the blood vessels. Angiogram technology is commonly employed to guide catheters and needles. Angiograms can also be used to examine, in a non-invasive manner, cessation or rate of blood flow, or sealing of such a breach or puncture (Hoekstra et al., 1998, Biomaterials. 19:1467-1471). CT or MRI imaging can also be used to examine sealing of a hemodialysis needle wound site and cessation of blood from the wound, blood flow through the vascular access site, stenosis, or development of vascular access complications.

4.2.6.3. Ultrasonography

Various sonography and ultrasonography techniques may be employed with the methods of the invention to examine bleeding and/or clotting at the site of removal of hemodialysis needles or bleeding and/or presence of a vascular access complication at a vascular access site. Duplex ultrasonography has demonstrated useful clinical applications in peripheral arterial testing for lesion localization and quantification of abnormal blood flow. For example, color flow duplex sonography of a puncture wound site can be used to test for blood clotts, pseudoaneurysm, and A-V fistula formation (Gwechenberger et al., 1997, Angiology. 48(2):121-126).

4.3. Composition Dosage and Administration

Generally, a therapeutically effective amount, will vary with the patients age, condition, and sex, as well as the nature and extent of the condition in the subject, all of which can be determined by one of ordinary skill in the art. A therapeutically effective amount is an amount of composition that achieves hemostasis in about one to about fourteen minutes, with compression. For example, the effective dose (i.e., amount) needed for an infant may differ from an elderly patient. The actual amount and formulation of the composition to be administered will depend on various factors such as the severity of the wound, the condition of the patient, the age of the patient and any collateral injuries or medical ailments possessed by the patient. For example, ESRD patients often have cardiac disease, compromised vascular systems, hypertension, hypotension, diabetes mellitus, polycystic kidney disease, glomeralonephritis or infections diseases, e.g., HIV or hepatitis.

Toxicity and efficacy of the compositions of the invention can be determined by standard pharmaceutical procedures in cell cultures or experimental animals, e.g., for determining the ED50 (the dose therapeutically effective in 50% of the population). Compositions that exhibit greater therapeutic effect are preferred. In the present instance, compositions that exhibit toxic side effects may be used in carrying out the methods of the invention. The potential damage to unaffected cells is minimized, since the compositions are applied to the site of affected tissue and thereby reduce the risk of side effects.

The data obtained from the cell culture assays and animal studies can be used in formulating a range of dosage for use in humans. The dosage of such compositions lies preferably within a range of concentrations that include the ED50. The dosage may vary within this range depending upon the formulation of the composition, i.e., gel, foam, patch, etc. For any vasoconstrictor used in the method of the invention, the therapeutically effective dose can be estimated initially from tissue or tissue culture assays.

One standard tissue assay is conducted using aortic rings excised from rats. The aorta are then rapidly suspended in a warmed Krebs-Henseleit (KH) buffer consisting of (in mmol/l): 118 NaCl, 4.75 KCl, 2.54 $CaCl_2.2H_{20}$, 1.19 $KH_2PO_4$, $1.19MgSO_4.7H_2O$, 12.5 $NaHCO_3$, and 10.0 glucose. Isolated vessels can be carefully freed of connective tissue and cut into rings 2-3 mm in length. The rings are then mounted on stainless steel hooks, suspended in a 10-ml tissue bath, and connected to Fr-03 force displacement transducers (Grass Instrument, Quincy, Mass.) to record changes in force on a Grass model 7 oscillographic recorder. The baths are filled with KH buffer and aerated at 37° C. with 95% $O_2$+5% $CO_2$. A resting force of 0.5 g is applied to the SMA rings, and then the rings are equilibrated for 90 minutes. During this period, the buffer in the tissue bath is replaced every 15-20 minutes, and the resting force of the vascular rings is adjusted until 0.5 g of pre-load is maintained. After 90 to 120 minutes of equilibration, the rings are exposed to 100 nM U-46619 (9,11-dideoxy-9α-11α-methaneepoxy-prostagalandin $F_{2α}$, Biomol Research Laboratories, Plymouth Meeting, Pa.), a thromboxane $A_2$ mimetic, to generate 1.0 g of developed force. Once a stable contraction is obtained, acetylcholine, a typical endothelium-dependent vasodilator, is added to the bath in cumulative concentrations of 0.1, 1, 10, and 100 nM to assess the integrity of endothelium. After the cumulative response is stabilized, the rings are washed and again allowed to equilibrate to baseline. Once a stabilized baseline response is obtained one skilled in the art can proceed to test various vasoconstrictors by repeating the procedure.

The function of a coagulant can be tested by standard assays. In such assays, normal human blood, without anticoagulant, is drawn and placed in several test tubes. For Example, the normal blood, without a composition of the invention, is allowed to clot (usually within about 10 minutes). Other samples of normal blood are drawn and one milliliter aliquots are placed in test tubes with descending aliquots of a particular composition of the invention for which one desires to test coagulant properties. Variations on this standard assay can be conducted where the patient has had an anticoagulant introduced into the bloodstream prior to withdrawal of blood. The results can be used to identify compositions of the invention that can accelerate hemostasis, i.e. cessation of flow of blood from a wound.

In various embodiments, an amount of vasoconstrictor and/or coagulant tested for effectiveness is an amount that is about 0.5-fold, 0.75-fold, 1-fold, 2-fold, 3-fold, 4-fold, 5-fold, 10-fold, 12-fold, 15-fold, 20-fold, 50-fold or 100-fold of effective dosage that can be used in the present methods.

In certain embodiments of the invention, an effective amount of a vasoconstrictor and/or coagulant is an amount that results in reduction or cessation of bleeding when applied to a catheter exits wound without compression. In other embodiments of the invention, an effective amount of a vasoconstrictor and/or coagulant is an amount that results in reduction or cessation of bleeding when applied to a catheter exits wound with compression according to the methods of the invention.

In embodiments of the invention where the composition of the invention is formulated as, embedded in, or applied to a patch, 100 mg of the composition may be present in 1 $cm^2$ of the wound-contacting surface of the patch. In other embodiments, the effective amount of a composition of the invention present in 1 $cm^2$ of a patch can be about 0.05 mg, 0.10 mg, 0.25 mg, 0.50 mg, 0.75 mg, 1 mg, 2 mg, 5 mg, 8 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, or 2000 mg of the composition, wherein the composition has a concentration between about 1 mM and 70 mM. In a preferred embodiment, wherein the composition comprises p-GlcNAc, the effective amount of a p-GlcNAc present in 1 $cm^2$ of a patch is between 3 mg and 20 mg of the composition.

One skilled art would readily be able to determine the amount of a vasoconstrictor and/or a coagulant effective to achieve hemostasis and reduce the need for compression. For example, standard doses and methods for determining dosage of drugs are described in the Physicians' Desk Reference (Medical Economics Company, Inc., Montvale, N.J., 2000,) which is incorporated by reference herein in its entirety. The methods described in section 4.2.5. for calculating hemostasis time by observing blood flow at time intervals can also be used to determine whether a specific amount of a specific vasoconstrictor and/or a specific coagulant is an effective amount such that one applying compression can do so for about one to fourteen minutes, and achieve hemostasis.

In other embodiments, where the composition of the invention is formulated as, embedded in, or applied to a patch, 100 μg of the composition may be present in 1 $cm^2$ of the wound-contacting surface of the patch. In other embodiments, the effective amount of a composition of the invention present in 1 $cm^2$ of a patch can be about 5 μg, 10 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 105 μg, 110 μg, 115 μg, 120 μg, 125 μg, 130 μg, 135 μg, 140 μg, 145 μg, 150 μg, 155 μg, or 160 μg of the composition, wherein the composition has a concentration between about 1 mM and 70 mM. An example of a coagulant that can be effective in such amounts is thrombin. An example of a vasoconstrictor that can be effective in such amounts is endothelin-1.

In yet other embodiments, the effective amount of a composition of the invention is about 1-1000 IU/$cm^2$ wherein the composition is formulated as, embedded in, or applied to a patch.

In certain embodiments, an effective amount of a composition of the invention is an amount that activates hemostasis in the presence of a coagulant or an anticoagulant.

In certain embodiments, the effective dose is the dose necessary to initiate clotting with or without compression. In other embodiments, the effective dose is the dose necessary to cause formation of a firm clot that will remain with or without compression. In yet other embodiments, an effective dose can be determined by the strength of the clot, i.e. the time for which the clot holds with or without compression.

Once it has been determined how varying concentrations and amounts of a particular vasoconstrictor and/or coagulant act in vitro, effective vasoconstrictors and/or coagulants can be further tested in animal models by methods. A series of measurements can be taken varying the concentration or amount of the vasoconstrictor and/or coagulant to determine an effective amount. Such series of measurements can be used to predict how a particular vasoconstrictor and/or coagulant will function and allow for a determination of effective amount for a patient. Such information can be used to more accurately determine useful doses in humans.

Results from animal models can be extrapolated to determine effective doses for human subjects. Comparing varying concentrations of a vasoconstrictor and/or coagulant in one or more animal models allows for the establishment of dose response curves that can be used to estimate effective amounts in a human, given the particular circumstances of each subject, i.e., size of wound, age of patient, presence of coagulants or anticoagulants in the blood stream.

Ultrasound imaging or Doppler flow analysis of the vascular access site allows for the determination of cessation or reduction of blood flow through the skin surface wound or vascular access site. If blood flow through the vascular access site is inhibited for prolonged periods of time, i.e., greater than about fourteen minutes, it may cause vascular access complications. Thus, Doppler flow and ultrasound would allow for a determination of the maximum upper limit of an effective amount of a vasoconstrictor and/or coagulant. For example, if the effect of a coagulant extends into the blood vessel and causes clotting of platelet and cessation of blood within the blood vessel, the effect could be damaging. In another embodiment, the maximum upper limit of an effective amount of a vasoconstrictor and/or coagulant can be measured as the amount of the composition of the invention that causes a cessation of blood flow through the vascular access site in the presence or albescence of compression for about one to fourteen minutes.

4.4. Kits

A kit is also provided which according to the invention comprises any of the above described embodiments. The kit can include the composition contained within a sealed, water proof, sterile package which facilitates removal of the composition without contamination. Materials from which containers may be made include aluminum foil, plastic, or another conventional material that is easily sterilized. The kit can contain a single composition or multiple compositions, preferably wherein each is provided in a separate, waterproof, sterile package. In one embodiment, the kit can include the composition contained within a plastic or metal tray or container with one or more compartments that provides a barrier to moisture.

In another embodiment, a container having dual compartments is provided. A first compartment contains the composition, while the second compartment contains a topical barrier, membrane, or film according to the invention. In field use, the barrier, membrane, or film can be readily dipped into an opened first compartment and subsequently applied to the hemodialysis needle wound. The composition can be applied or added to a topical barrier, membrane, or film prior to being packaged and sterilized or the composition can be formulated as a barrier, membrane, or film. In another embodiment, the kit may not contain a barrier, membrane, or film if the composition is not formulated as such.

According to one aspect of the invention, various specialized kits can be provided. The kit can contain multiple compositions of the invention, wherein each is contained within a separate sealed sterile package or container. The kit can contain in one or more containers, a an effective amount of a vasoconstrictor, while in another separate container a pharmaceutically acceptable carrier can be packaged. In a separate container the kit can contain a neutral liquid, neutral gel or neutral solid. The kit may also contain a coagulant in accord with the composition for use in the methods of the invention as described herein.

The kit can comprise a composition that can be formulated as a barrier-forming material that forms a barrier to blood. The kit can comprise a composition that can coat, be added to, or integrated into a barrier-forming material that forms a barrier to blood. In one embodiment a kit comprises a pharmaceutical composition comprising a patch made of barrier-forming materials that are embedded with one or more coagulant and/or vasoconstrictor agent(s). In one embodiment a kit comprises a pharmaceutical composition comprising a gauze embedded with one or more coagulant and/or vasoconstrictor agent(s). In certain embodiments, a kit comprises pharmaceutical compositions comprising a barrier-forming material embedded or combined with one or more coagulant and/or vasoconstrictor agent(s), wherein the barrier-forming material contains an adhesive so that the material can be adhere to a patient's skin surface. Alternatively, a kit lacks barrier-forming materials.

In one embodiment a kit comprises a patch embedded or coated with a vasoconstrictor, a coagulant, or an agent that functions as both a vasoconstrictor or coagulant. In another embodiment a kit comprises a gel that can be used in the methods of the invention, wherein the gel comprises a vasoconstrictor, a coagulant, or an agent that functions as both a vasoconstrictor or coagulant.

In a preferred embodiment the kit contains gauze.

A kit can comprise a notice regarding FDA approval and/or instructions for use in combination with compression during hemodialysis sessions. The instructions can recite a method for reducing vascular access complications. In one embodiment, the instructions recite applying topically to a hemodialysis vascular access site during a hemodialysis session a composition comprising an amount of a vasoconstrictor or coagulant effective for reducing post-hemodialysis bleeding at the vascular access site, and applying compression to the hemodialysis vascular access site for a period of about one to fourteen minutes. The instructions can also recite post procedural instructions, warnings, precautions, and/or indications of market clearance or approval. The instructions can also recite instructions for labeling the kit and/or kit components.

In one embodiment, the kit comprises instructions for topically applying the composition at a hemodialysis vascular access site where compression is applied for about one to fourteen minutes, resulting in a reduction in vascular access complications.

In another embodiment, the kit comprises instructions for topically applying the composition with compression at a hemodialysis vascular access site to achieve a cessation or reduction of blood flow out of the hemodialysis vascular access site in about one to fourteen minutes.

5. EXAMPLES

5.1. Example 1

Use of the Healtekpatch™ to Promote Rapid Wound Closure and Cessation of Bleeding in Hemodialysis Patients Example 1 is directed toward a study testing the utility of a particular material, HealTekPatch™, as a device to promote rapid wound closure and cessation of bleeding from such vascular access sites in hemodialysis patients following needle removal. HealTekPatch™ comprises fully-acetylated poly-N-acetyl glucosamine ("p-GlcNAc"). The polymer p-GlcNAc and derivatives and formulations thereof has been described in U.S. Pat. Nos. 5,622,834; 5,623,064; 5,846,952; 5,624,679; 5,858,350; 5,635,493; 5,686,115; 6,063,911; and 5,510,102.

The focus of the initial test of this example, was directed toward a randomly-selected group of 25 hemodialysis patients from within a total pool of 66 patients who had met the inclusion criteria and who had signed a consent form. In this study, each patient served as his/her own control.

As indicated by the data provided below, HealTekPatch™ proved more effective than the gauze control in 86% of the patients tested. In addition, use of HealTekPatch™ stopped bleeding within 5 minutes in 72% (18 of 25) of patients. Standard care (gauze) stopped bleeding within 5 minutes in only 16% (4 of 25) of patients. Furthermore, within the subset of patients treated with prophylactic anticoagulants, use of HealTekPatch™ was more effective than the gauze control for rapid wound closure and cessation of bleeding in 88% of the patients.

5.1.1. Materials

HealTekPatch™, (Marine Polymer Technologies, Danvers, Mass.) a fully-acetylated poly-N-acetyl glucosamine (p-GlcNAc), is a highly purified polysaccharide free of protein and other contaminants, see Section 4.1.4. Biological testing of the HealTekPatch™ device was carried out at Toxikon Laboratory (Woburn, Mass.), and included the following tests: Cytotoxicity, Primary Skin Irritation, Sensitization Assay, Systemic Toxicity, Hemocompatibility, Pyrogenicity, Implantation Test, Mutagenicity, and Subchronic Toxicity. HealTekPatch™ is fully biocompatible and non-toxic, as indicated by United States Food and Drug Administration (FDA) Tripartite Biocompatibility Guidance Tests. The gauze used was Medical 2"×2" 4 ply (Johnson & Johnson, New Brunswick, N.J.). The gauze was folded to form a 1"×1" (2.5 cm×2.5 cm) square.

5.1.2. Patient Selection Method

Twenty-five patients were randomly selected for inclusion in the present study from among the 66 hemodialysis-patient population on record at a given date at Dialysis Clinic Inc. (Boston, Mass.).

Patients were offered the opportunity to participate in the study when they appeared for their routine hemodialysis treatments. A patient was deemed eligible for the present study if he or she: (1) was over 18 years of age and able to give consent, (2) was dialyzed via native vein fistula or via polytetrafluoroethylene graft, and (3) had bled for more than 5 minutes after removal of hemodialysis needles in a prior, observational study. Patients with antibodies to HIV or with Hepatitis B surface antigen were excluded from the study. Also excluded were patients enrolled in other clinical trials. Table 1 summarizes the demographics of the twenty five patients enrolled in the present study.

TABLE 1

| Sex | | | Vascular Access | | |
|---|---|---|---|---|---|
| Female | 11 | 44% | Fistula | 15 | 60% |
| Male | 14 | 56% | Graft | 10 | 40% |

| Age | | | Concurrent Diseases | | |
|---|---|---|---|---|---|
| Under 60 | 6 | 24% | Diabetes | 6 | 24% |
| 60-69 | 7 | 28% | Hypertension | 6 | 24% |
| 70-79 | 5 | 20% | None | 13 | 52% |
| Over 80 | 7 | 28% | | | |

TABLE 1-continued

| Race | | | Concurrent Daily Prophylactic Anticoagulation Therapy | | |
|---|---|---|---|---|---|
| Asian | 6 | 24% | aspirin | 6 | 24% |
| Black | 7 | 28% | Ecotrin | 3 | 12% |
| Hispanic | 1 | 4% | Warfarin | 4 | 16% |
| White | 11 | 44% | None | 12 | 48% |

Patient evaluation included a review of the patient's clinical history and medical chart as well as an inspection of the vascular access site, in order to ensure that the patients chosen met study inclusion criteria. This patient evaluation also provided relevant clinical data for each patient, which included: skin condition, the pattern of needle punctures, the type of vascular access, heparin doses, venous pressures, blood flows, adequacy of dialysis, nutritional status, hematologic parameters, use of oral anticoagulation or antiplatelet therapy and a history of repairs to and replacements of the vascular access. The results of each patient's blood tests, which included the most recent complete blood count and platelet count, were copied from each patient's medical chart.

5.1.3. Treatment Method

Each patient served as his/her own control. Each patient was treated once with the HealTekPatch™, and once with a gauze control (standard treatment) to determine which method stopped bleeding faster. The order in which each material (HealTekPatch™ disk or gauze square) was used, was randomized for each patient. Following removal of the dialysis needles, the selected material (either a 1.5 cm HealTekPatch™ disk or a 2.5 cm square of gauze) was applied to each needle site. Each material was held in place, with firm digital pressure, for 5 minutes, after which digital pressure was removed, taking care not to remove the test material. Each site was observed for a period of 2 minutes. If bleeding was noted within this 2-minute observation period, digital pressure was immediately reapplied for an additional 5 minutes. This process was repeated until cessation of bleeding was achieved. The number of applications of pressure needed for cessation of bleeding was recorded to a maximum of three applications. If bleeding was not stopped within 15 minutes of treatment (i.e. three 5-minute pressure applications), the data was no longer recorded and compression resumed until the bleeding stopped for that patient. The bleed time was defined as the period of time beginning with removal of the needle from a site and ending when bleeding from that site had stopped. Arterial and venous bleed times were recorded separately and the longer of the two time periods was considered to be the bleed time for the particular treatment. The results of this clinical trial are summarized in Table 2, below.

TABLE 2

CLINICAL TRIAL RESULTS

| PATIENT NUMBER | TIME (MIN) TO CESSATION OF BLEEDING USING: | | TREATMENT PROVIDING IMPROVED RESULTS |
|---|---|---|---|
| | PATCH | GAUZE | |
| 1 | 5 | 10 | HealTekPatch ™ |
| 2 | 5 | 15 | HealTekPatch ™ |
| 3 | 10 | 15+ | HealTekPatch ™ |
| 4 | 5 | 15 | HealTekPatch ™ |
| 5 | 15 | 15+ | HealTekPatch ™ |
| 6 | 5 | 5 | Tie* |
| 7 | 5 | 15+ | HealTekPatch ™ |

TABLE 2-continued

CLINICAL TRIAL RESULTS

| PATIENT NUMBER | TIME (MIN) TO CESSATION OF BLEEDING USING: | | TREATMENT PROVIDING IMPROVED RESULTS |
|---|---|---|---|
| | PATCH | GAUZE | |
| 8 | 10 | 10 | Tie |
| 9 | 5 | 10 | HealTekPatch ™ |
| 10 | 5 | 15 | HealTekPatch ™ |
| 11 | 15 | 10 | Gauze |
| 12 | 10 | 15+ | HealTekPatch ™ |
| 13 | 10 | 15 | HealTekPatch ™ |
| 14 | 5 | 5 | Tie* |
| 15 | 5 | 10 | HealTekPatch ™ |
| 16 | 10 | 15 | HealTekPatch ™ |
| 17 | 5 | 10 | HealTekPatch ™ |
| 18 | 5 | 5 | Tie* |
| 19 | 5 | 10 | HealTekPatch ™ |
| 20 | 5 | 10 | HealTekPatch ™ |
| 21 | 5 | 5 | Tie* |
| 22 | 5 | 10 | HealTekPatch ™ |
| 23 | 5 | 10 | HealTekPatch ™ |
| 24 | 5 | 10 | HealTekPatch ™ |
| 25 | 5 | 15 | HealTekPatch ™ |

Tie* 4 of 5 tie scores occurred in the initial 5 minutes of pressure.
Observation of events occurring in the initial 5 minutes were beyond the scope of the protocol.

5.1.4. Summary of Results

As demonstrated in Table 2, above, bleeding times in 19 of 25 patients were shorter using HealTekPatch™ in comparison to gauze. With respect to the remaining six patients, bleeding times were the same using either HealTekPatch™ or gauze for 5 patients while the bleeding time observed was longer for only one patient using HealTekPatch™ as compared to the use of the control material, gauze.

In addition, it was noted that, surprisingly, it was possible to stop bleeding in less than 15 minutes in the majority of instances using either HealTekPatch™ or gauze. This is in contrast to standard procedure for hemodialysis patients, which comprises applying compression for at least 15 minutes stop bleeding.

5.1.5. Data Analysis
5.1.5.1. Statistical Evaluation

The data obtained in the clinical trial described above, were analyzed by personnel of the Biostatistics Research Center, New England Medical Center (Boston, Mass.), as described below.

For purposes of the initial analysis, each tie was counted as a one-half success. Accordingly, this analysis was based upon 21.5 successes out of 25 trials. This leads to an estimated effectiveness of 86% with an exact binomial confidence interval of (68%, 96%). A plot of the cumulative proportion of success for this distribution shows that there is less than a 1 in 100 chance that the success rate is less than about 2 in 3. A plot of the posterior distribution of the success proportion was generated using a Bayesian analysis based on a noninformative Beta prior distribution, and showed that the data most likely support a success rate of 86%. This analysis further indicated that a rate less than 70% is unlikely while a rate of success of 95% is certainly possible.

5.1.5.2. Sensitivity Analysis

A second, more conservative analysis was also carried out in which ties were treated as failures. This analysis provided a success rate of 76% (19 in 25), with an exact confidence interval for this rate of (56%, 92%). Even this conservative analysis shows that there is almost no possibility that use of HealTekPatch™ is not as effective as the gauze control in promoting cessation of bleeding from a vascular access site after needle removal.

In a third analysis of the data obtained in the clinical study disclosed above, four of the ties (i.e., those in which bleeding had been arrested within the first five-minute test period) were eliminated, while the fifth tie was deemed a failure. In this instance, the success rate was 93% (19.5 out of 21) with an exact 95% confidence interval of (76%, 100%).

5.1.5.3. Wound Closure Using HealTekPatch™

The data of Table 2 demonstrate that application of the HealTekPatch™ stopped bleeding within five minutes for 72% (18 of 25) patients, while the control, standard application of a gauze square stopped bleeding within five minutes only 16% (4 or 25) patients.

5.1.5.4. Statistical Analysis of Wound Closure Using HealTekPatch™

Using the HealTekPatch™ as described in the previous section (5.1.5.3), there were 18 successes out of 25 trials. This leads to an estimated effectiveness of 72% with an exact binomial confidence interval of (52%, 84%). In contrast, using the standard gauze treatment provided only 4 successes out of 25 trials. This leads to an estimated effectiveness of 16% with an exact binomial confidence interval of (0%, 28%).

5.2. Example 2

Use of the Healtekpatch™ to Promote Rapid Wound Closure and Cessation of Bleeding in Hemodialysis Patients on Prophylactic Anticoagulant Therapy Within the set of 25 patients enrolled in the clinical study described in Example 1, above, there was a subset of 13 patients who were also being treated with prophylactic anticoagulants (aspirin, Ecotrin, or Warfarin). As demonstrated below, rapid wound closure and cessation of bleeding from vascular access sites was more effectively achieved by application of HealTekPatch™ discs than by application of gauze squares.

This conclusion is based upon a review of the bleeding-time data obtained for the subset of 13 anticoagulant-treated patients of the clinical study of Example 1, above. Accordingly, the materials and treatment methods of Example 2 are those described in Sections 5.1.1 and 5.1.3 of Example 1, above.

5.2.1. Summary of Results

Table 3 summarizes the results obtained in the clinical study described above for that subset of patients who were being treated with additional anticoagulation therapy.

TABLE 3

| PATIENT NUMBER | ADDITIONAL ANTICOAGULANT ADMINISTERED | TIME (MIN) TO CESSATION OF BLEEDING USING: | | TREATMENT PROVIDING IMPROVED RESULTS |
|---|---|---|---|---|
| | | PATCH | GAUZE | |
| 1 | Aspirin | 5 | 10 | HealTekPatch ™ |
| 3 | Ecotrin | 10 | 15+ | HealTekPatch ™ |
| 6 | Aspirin | 5 | 5 | Tie* |
| 7 | Ecotrin | 5 | 15+ | HealTekPatch ™ |
| 8 | Warfarin | 10 | 10 | Tie |
| 10 | Warfarin | 5 | 15 | HealTekPatch ™ |
| 13 | Aspirin | 10 | 15 | HealTekPatch ™ |
| 16 | Aspirin | 10 | 15 | HealTekPatch ™ |
| 17 | Ecotrin | 5 | 10 | HealTekPatch ™ |

TABLE 3-continued

| PATIENT NUMBER | ADDITIONAL ANTICOAGULANT ADMINISTERED | TIME (MIN) TO CESSATION OF BLEEDING USING: | | TREATMENT PROVIDING IMPROVED RESULTS |
|---|---|---|---|---|
| | | PATCH | GAUZE | |
| 18 | Aspirin | 5 | 5 | Tie* |
| 22 | Aspirin | 5 | 10 | HealTekPatch ™ |
| 24 | Warfarin | 5 | 10 | HealTekPatch ™ |
| 25 | Warfarin | 5 | 15 | HealTekPatch ™ |

(Tie*: Two of the three tie scores occurred in the initial 5 minutes of pressure).
Observation of events occurring in the initial 5-minute time period were beyond the scope of the protocol followed in this clinical study, as described above in Section 5.1.3.

As indicated in Table 3, bleeding times were shorter when a HealTekPatch™, rather than a gauze square was applied to vascular access sites after needle removal at the end of a hemodialysis treatment session in 10 of 13 patients identified as being treated with prophylactic anticoagulant therapy. Moreover, for the remaining 3 patients of this anticoagulant-treated subset of patients, bleeding times were the same (i.e. designated as a tie) whether a HealTekPatch™ or a gauze square was applied to the vascular access site after hemodialysis.

5.2.2. Data Analysis

Statistical evaluation of the results of Experiment 2 was performed using the methods described above in Section 4.5.1, and counting a tie as one-half success. According to this analysis, there were 11.5 successes out of 13 trials, which leads to an estimated effectiveness of 88% with an exact binomial confidence interval of (62%, 100%).

5.2.3. Conclusion

The clinical study described above in Examples 1 and 2 demonstrates that HealTekPatch™ is very effective in reducing the duration of postdialysis bleeding from vascular access sites of hemodialysis patients. Treatment using HealTekPatch™ proved more effective than treatment with the control material, gauze, in 86% of the patients tested. Use of HealTekPatch™ material stopped bleeding within 5 minutes in 72% (18 of 25) patients, while the standard care (treatment with gauze) stopped bleeding within 5 minutes in only 16% (4 of 25) patients. Moreover, in the subset of patients treated with prophylactic anticoagulants, treatment using HealTekPatch™ was more effective than use of the gauze control, for rapid wound closure and cessation of bleeding in 88% of the patients treated. These results verify that the HealTekPatch™ promotes rapid wound closure and cessation of bleeding in hemodialysis patients as well as for patients on prophylactic anticoagulation therapy. Accordingly, use of HealTekPatch™ as described above, will facilitate earlier patient ambulation and return to the home environment.

5.3. Example 3

Use of Hemostatic Compositions in Conjunction With the Methods of the Present Invention to Promote Rapid Wound Closure and Cessation of Bleeding in Hemodialysis Patient 5.3.1. Introduction The standard method for achieving hemostasis at vascular access sites of patients after hemodialysis treatment involves application of a gauze pad, with pressure, until bleeding stops. In many instances, this pressure must be applied for a period of 15 to 20 minutes, and standard procedures utilize at least 15-20 minutes of compression. However, as demonstrated in the data provided below, an extended period of compression (i.e. greater than 14 minutes), correlates with vascular access complications, which are referred to as "vascular events." That is, patients who require a longer time to control post-hemodialysis bleeding will experience a greater number of vascular access complication events than those who need pressure applied for a shorter period of time. Accordingly, use of treatments that reduce the length of time needed to achieve post-hemodialysis hemostasis, such as those described in Examples 1 and 2, above, will significantly decrease the incidence of vascular access complications and therefore will extend the lifetime and improve the patency rates of both primary arteriovenous fistulae and synthetic grafts. Reduction in access complications will lead to major cost savings. As noted above, such vascular access complications are the single greatest cause of morbidity within the hemodialysis patient population requiring expensive, extended medical attention and inpatient care.

5.3.2. Data Collection

The data of Table 4, below, were assembled over an eight-month observation period directed toward the 66 patients identified in Example 1 above, and were collected from both physical and electronic charts for each patient. Electronic chart data included that entered in operating room notes, special procedure notes, radiology results, and discharge summaries. Each patient's postdialysis compression time was checked twice in one week, every week, every other month for the eight-month period of the study. Postdialysis compression time was defined as extending from removal of the first needle until the cessation of bleeding at both sites. Concurrent patient data on hematocrit, albumin, platelet count KTV, PCRN, blood flow, and venous pressure were collected for each patient to insure that there had been no physical change in the patient's health status.

TABLE 4

| Patient Number | Compression Time (in minutes) | Months on Dialysis | Number of Vascular Events |
|---|---|---|---|
| 24 | 6.1 | 37.3 | 0 |
| 2 | 6.2 | 37.5 | 0 |
| 65 | 6.6 | 20.5 | 0 |
| 63 | 6.7 | 23.4 | 0 |
| 56 | 6.7 | 41.0 | 2 |
| 3 | 6.8 | 84.5 | 0 |
| 20 | 8.3 | 73.2 | 0 |
| 40 | 8.3 | 13.6 | 0 |
| 7 | 9.0 | 19.6 | 0 |
| 44 | 9.2 | 13.5 | 0 |
| 37 | 9.3 | 4.1 | 0 |
| 47 | 9.3 | 17.3 | 1 |
| 53 | 9.5 | 5.1 | 0 |
| 41 | 10.0 | 16.4 | 0 |
| 8 | 10.5 | 29.5 | 1 |
| 50 | 10.5 | 18.9 | 1 |
| 6 | 10.6 | 36.2 | 1 |
| 17 | 10.6 | 35.0 | 4 |
| 25 | 10.9 | 28.6 | 1 |
| 9 | 11.1 | 37.3 | 1 |
| 62 | 11.5 | 46.9 | 2 |
| 66 | 11.8 | 20.9 | 1 |
| 22 | 12.0 | 31.0 | 3 |
| 52 | 12.2 | 27.6 | 0 |
| 45 | 12.3 | 34.5 | 0 |
| 54 | 12.3 | 11.2 | 0 |
| 27 | 12.7 | 38.7 | 0 |
| 16 | 13.3 | 9.2 | 0 |
| 10 | 14.0 | 12.5 | 1 |
| | | Total: 812.5 | Total: 15 |
| 58 | 14.1 | 24.4 | 1 |
| 34 | 14.2 | 16.7 | 0 |
| 35 | 15.2 | 8.3 | 0 |
| 49 | 15.2 | 35.5 | 0 |

TABLE 4-continued

| Patient Number | Compression Time (in minutes) | Months on Dialysis | Number of Vascular Events |
|---|---|---|---|
| 61 | 15.2 | 13.4 | 2 |
| 31 | 15.5 | 49.2 | 1 |
| 55 | 15.8 | 23.1 | 2 |
| 38 | 15.8 | 49.2 | 3 |
| 42 | 16.0 | 38.3 | 0 |
| 36 | 16.1 | 29.7 | 3 |
| 15 | 16.2 | 27.5 | 0 |
| 46 | 16.2 | 17.4 | 0 |
| 57 | 16.3 | 42.5 | 1 |
| 39 | 16.7 | 16.4 | 0 |
| 51 | 16.7 | 56.0 | 4 |
| 12 | 17.1 | 51.4 | 1 |
| 59 | 17.7 | 64.5 | 3 |
| 4 | 18.3 | 41.6 | 0 |
| 28 | 18.3 | 33.5 | 1 |
| 33 | 18.5 | 40.5 | 1 |
| 43 | 18.8 | 31.6 | 2 |
| 26 | 19.1 | 31.1 | 2 |
| 5 | 20.5 | 18.4 | 0 |
| 14 | 20.5 | 39.1 | 1 |
| 18 | 20.6 | 22.8 | 2 |
| 21 | 20.8 | 27.0 | 1 |
| 29 | 21.0 | 15.7 | 2 |
| 60 | 22.2 | 36.3 | 1 |
| 1 | 22.3 | 47.0 | 2 |
| 30 | 22.5 | 14.8 | 0 |
| 13 | 22.6 | 11.2 | 1 |
| 32 | 22.8 | 32.5 | 1 |
| 19 | 24.1 | 18.8 | 0 |
| 64 | 26.0 | 8.4 | 1 |
| 23 | 27.1 | 18.5 | 0 |
| 18 | 34.3 | 31.5 | 0 |
| 11 | 48.0 | 33.4 | 1 |
|  |  | Total: 1129.7 | Total: 38 |

5.3.3. Summary of the Data Correlating Compression Time and Frequency of Vascular Events The average compression time required to control postdialysis bleeding was observed to be 15.5 minutes. Surprisingly, 69.5% of the vascular access events, i.e., vascular access complications, occurred in those patients requiring compression for more than 14 minutes. More specifically, the data of Table 4 indicate that a total of 18 vascular events were noted within a total of 812.5 months of medical care of 29 patients requiring less than 14 minutes of standard treatment to achieve hemostasis subsequent to a dialysis session. In contrast, the data of Table 4 indicate that a total of 41 vascular events were noted within a total of 1129.7 months of medical care of the remaining 37 patients in the study who required 14 minutes or longer of standard treatment to achieve hemostasis subsequent to a dialysis session. The 63.6% increase [(41/1129.7)/(18/812.5)] in the incident rate of vascular event occurrences per month for those patients requiring at least 14 minutes of compression is striking.

Accordingly, treatment methods, such as those described in Examples 1 and 2 above, that would decrease the length of time of compression required to achieve hemostatis within the patient population requiring 14 minutes or more of compression to achieve hemostatis, would decrease the number of vascular events observed over the long term. In addition, the treatment methods, such as those described in Examples 1 and 2 above, that would decrease the length of time of compression required to achieve hemostatis within the patient population requiring 10 minutes or more of compression to achieve hemostatis, would also decrease the number of vascular events observed over the long term.

5.3.4. Discussion

The results of the experiments presented hereinabove demonstrate, first, that the length of compression time at the site of hemodialysis needle punctures is the cause of vascular access complications, and second, that the length of compression time needed to cease or reduce bleeding can be reduced by application of the methods of the invention.

One of ordinary skill in the art would not have expected a reduced compression time at the site of removal of hemodialysis needles for about one to fourteen minutes could reduce vascular access complications at the site where the vein and artery have been sutured or where the synthetic graft is connected to the blood vessels.

It is counterintuitive to expect a direct correlation between vascular access complications and the extent, i.e. amount or length, of compression. This is particularly true for vascular access complications at the site where the artery and vein have been connected in an AV fistulae or the site of attachment of graft. The primary cause of access failure is thrombosis and longer compression is indicative of coagulopathy. Furthermore, the generally accepted pathology associated with vascular access failure has been found to be intimal hyperplasia at the venous anastamosis site not at the cannulation site. Thus, one of ordinary skill in the art of hemodialysis would not expect to obtain a direct and quantitative relationship between the length of time pressure is applied to a vascular access site to control bleeding and the number of vascular access complications in hemodialysis patients.

While applying excessive or prolonged compression to the site where the hemodialysis needles have been removed is known to cause thrombosis and other vascular complications at the site where compression is applied it is surprising that reducing compression to about one to fourteen minutes, for the majority of hemodialysis sessions could reduce vascular access complications at the site where, for example, the A-V fistulae has been created or where the synthetic graft is connected to the blood vessels.

5.4. Example 4

Use of the Healtekpatch™ to Promote Rapid Wound Closure and Cessation of Bleeding in Eighty Hemodialysis Patients Example 4 is also directed toward a study testing the utility of a particular material, HealTekPatch™, as a device to promote rapid wound closure and cessation of bleeding from such vascular access sites in hemodialysis patients following needle removal.

The study presented in Example 4 differs from that of Example 1 in several aspects, including, but not limited to, the number of hemodialysis patients included in the study, and the method for timing cessation of bleeding. As indicated by the data provided below, HealTekPatch™ resulted in a 68% reduction in the average time required achieve cessation of bleeding.

5.4.1. Materials and Methods

HealTekPatch™, (Marine Polymer Technologies, Danvers, Mass.) a fully-acetylated poly-N-acetyl glucosamine (p-GlcNAc), is a highly purified polysaccharide free of protein and other contaminants, see Sections 4.1.4 and 5.1.1

5.4.1.1. Patient Selection

Eighty patients from four hemodialysis centers were monitored to assess the time required to obtain cessation of bleeding in hemodialysis patients and estimate reductions in vascular access complications. Patients were offered the opportunity to participate in the study when they presented for routine hemodialysis. The patients monitored met the following inclusion criteria: male and female age of 18 years and above, having chronic renal failure, undergoing chronic hemodialysis, functional vascular access as confirmed by Doppler examination, and having signed an Informed Consent Form. Patient evaluations were conducted the same as described for Example 1 to ensure that patients met study inclusion criteria and to collect relevant clinical data. (See Section 5.1.2).

5.4.2. Treatment Method

Each patient served as his/her own control receiving either a hemostatic patch or standard of care gauze control to achieve hemostasis. The order in which each material (HealTekPatch™ or gauze square) was used, was randomized for each patient. Following the removal of the dialysis needles, the randmoly selected treatment (either a HealTekPatch™ or gauze control) was applied to each needle site. These were held in place with firm digital pressure for 5 minutes. Then the digital pressure was removed, taking care not to remove the test material. The sites were observed for a period of 2 minutes. If bleeding recurred during the 2 minute period of observation, digital pressure was reapplied immediately for an additional 1 minute. This was repeated until cessation of bleeding was achieved. If the patient reached 30 minutes without hemostasis, the treatment was interrupted and assigned a value of 30. The time required for cessation of bleeding was recorded. The bleed time was considered the time from the removal of the needle until the site stopped bleeding. Arterial and venous bleed times were recorded separately and the longer of the two lengths of time was considered to be the bleed time for the particular treatment. Vascular Access Complications were estimated by applying the differential in time required to achieve hemostasis to the regression analysis described in Example 1.

5.4.3. Results

Results from the trial are presented in Table 5. The use of the HealTekPatch™ resulted in a 68% reduction in the average time required achieve cessation of bleeding. The time differences were statistically significant.

TABLE 5

| PATIENT | AGE | TIME (MIN) TO CESSATION OF BLEEDING USING | | TIME DIFFERENCE | |
|---|---|---|---|---|---|
| | | GAUZE | PATCH | MINUTES | % |
| 1 | 31 | 15 | 5 | 10 | 66.7% |
| 2 | 61 | 18 | 6 | 12 | 66.7% |
| 3 | 53 | 20 | 6 | 14 | 70.0% |
| 4 | 89 | 22 | 5 | 17 | 77.3% |
| 5 | 74 | 25 | 6 | 19 | 76.0% |
| 6 | 53 | 15 | 5 | 10 | 66.7% |
| 7 | 50 | 18 | 5 | 13 | 72.2% |
| 8 | 55 | 18 | 5 | 13 | 72.2% |
| 9 | 45 | 15 | 5 | 10 | 66.7% |
| 10 | 73 | 19 | 5 | 14 | 73.7% |
| 11 | 84 | 19 | 5 | 14 | 73.7% |
| 12 | 68 | 15 | 5 | 10 | 66.7% |
| 13 | 51 | 15 | 5 | 10 | 66.7% |
| 14 | 60 | 16 | 5 | 11 | 68.8% |
| 15 | 61 | 15 | 5 | 10 | 66.7% |
| 16 | 59 | 22 | 5 | 17 | 77.3% |
| 17 | 77 | 18 | 5 | 13 | 72.2% |
| 18 | 74 | 20 | 7 | 13 | 65.0% |
| 19 | 71 | 15 | 5 | 10 | 66.7% |
| 20 | 73 | 16 | 5 | 11 | 68.8% |
| 21 | 32 | 15 | 5 | 10 | 66.7% |
| 22 | 29 | 15 | 5 | 10 | 66.7% |
| 23 | 53 | 16 | 5 | 11 | 68.8% |
| 24 | 70 | 18 | 5 | 13 | 72.2% |
| 25 | 59 | 20 | 5 | 15 | 75.0% |
| 26 | 53 | 19 | 5 | 14 | 73.7% |
| 27 | 83 | 18 | 5 | 13 | 72.2% |
| 28 | 62 | 15 | 5 | 10 | 66.7% |
| 29 | 48 | 16 | 5 | 11 | 68.8% |
| 30 | 69 | 16 | 5 | 11 | 68.8% |
| 31 | 57 | 19 | 7 | 12 | 63.2% |
| 32 | 79 | 17 | 6 | 11 | 64.7% |
| 33 | 61 | 16 | 7 | 9 | 56.3% |
| 34 | 69 | 23 | 7 | 16 | 69.6% |
| 35 | 68 | 29 | 7 | 22 | 75.9% |
| 36 | 18 | 19 | 5 | 14 | 73.7% |
| 37 | 54 | 15 | 6 | 9 | 60.0% |
| 38 | 67 | 25 | 7 | 18 | 72.0% |
| 39 | 39 | 23 | 8 | 15 | 65.2% |
| 40 | 83 | 25 | 8 | 17 | 68.0% |
| 41 | 55 | 30 | 8 | 22 | 73.3% |
| 42 | 72 | 26 | 8 | 18 | 69.2% |
| 43 | 50 | 22 | 8 | 14 | 63.6% |
| 44 | 47 | 27 | 8 | 19 | 70.4% |
| 45 | 57 | 23 | 7 | 16 | 69.6% |
| 46 | 52 | 20 | 7 | 13 | 65.0% |
| 47 | 70 | 16 | 7 | 9 | 56.3% |
| 48 | 51 | 22 | 7 | 15 | 68.2% |
| 49 | 72 | 16 | 5 | 11 | 68.8% |
| 50 | 62 | 15 | 6 | 9 | 60.0% |
| 51 | 76 | 20 | 7 | 13 | 65.0% |
| 52 | 60 | 15 | 6 | 9 | 60.0% |
| 53 | 66 | 20 | 7 | 13 | 65.0% |
| 54 | 69 | 23 | 7 | 16 | 69.6% |
| 55 | 33 | 24 | 8 | 16 | 66.7% |
| 56 | 64 | 24 | 8 | 16 | 66.7% |
| 57 | 72 | 23 | 7 | 16 | 69.6% |
| 58 | 36 | 16 | 6 | 10 | 62.5% |
| 59 | 66 | 23 | 6 | 17 | 73.9% |
| 60 | 67 | 15 | 7 | 8 | 53.3% |
| 61 | 69 | 18 | 6 | 12 | 66.7% |
| 62 | 79 | 13 | 7 | 6 | 46.2% |
| 63 | 74 | 19 | 7 | 12 | 63.2% |
| 64 | 62 | 23 | 7 | 16 | 69.6% |
| 65 | 52 | 23 | 8 | 15 | 65.2% |
| 66 | 76 | 24 | 8 | 16 | 66.7% |
| 67 | 64 | 30 | 6 | 24 | 80.0% |
| 68 | 70 | 25 | 8 | 17 | 68.0% |
| 69 | 66 | 16 | 5 | 11 | 68.8% |
| 70 | 67 | 30 | 8 | 22 | 73.3% |
| 71 | 55 | 16 | 7 | 9 | 56.3% |
| 72 | 77 | 20 | 6 | 14 | 70.0% |
| 73 | 70 | 30 | 7 | 23 | 76.7% |
| 74 | 73 | 11 | 6 | 5 | 45.5% |
| 75 | 84 | 10 | 5 | 5 | 50.0% |
| 76 | 59 | 10 | 6 | 4 | 40.0% |
| 77 | 58 | 10 | 5 | 5 | 50.0% |
| 78 | 42 | 14 | 6 | 8 | 57.1% |
| 79 | 66 | 10 | 5 | 5 | 50.0% |
| 80 | 60 | 11 | 6 | 5 | 45.5% |
| average | | 19 | 6 | 13 | 68.4% |

All 80 patients exhibited a reduction in time to cessation of bleeding using the HealTekPatch™ in comparison to the control. The data in Table 5 also demonstrate that that application of the HealTekPatch™ stopped bleeding within five minutes for 40% (32 of 80) of patients, within 6 minutes for 60% (48 of 80) patients, and within 7 minutes for 85% (68 of 80) of patients.

5.4.4. Correlating Compression Time and Frequency of Vascular Events

To examine the relationship between compression time and vascular access complications, a Poisson regression model was constructed to relate the number of vascular access complications to the compression time required to achieve hemostasis. In this analysis the logarithm of the number of vascular access complication events per month was related to the compression time required for Blacks and non-Blacks separately by the following two equations:

log(events/month)=−7.042+0.367*compression time (non-Blacks)

log(events/month)=−6.737+0.367*compression time (Blacks)

The distribution of reductions in compression times were as follows: 29 patients of 80 (36%) exhibited reduced compression times from 11 minutes or greater to 5 minutes; 3 patients of 80 (3%) exhibited reduced compression times from 10 minutes to 5 minutes; 15 patients of 80 (18%) exhibited reduced compression times from 11 minutes or greater to 6 minutes; 1 patients of 80 (1%) exhibited reduced compression times from 10 minutes to 6 minutes; 20 patients of 80 (25%) exhibited reduced compression times from 11 minutes or greater to 7 minutes; and 12 patients of 80 (15%) exhibited reduced compression times from 11 minutes or greater to 8 minutes. Using the regression equations above, each of these 80 patients would be expected to have a proportionate reduction in numbers of vascular access complication events. The benefit for each patient was calculated as follows:

exp(0.367*#minutes reduced time less than 11 minutes).

Weighting by the distributions of time reductions gives the following geometric mean benefit:

exp{0.36*(0.367*6)+0.03*(0.367*5)+0.18*(0.367*5)+0.01*(0.367*4)+0.25*(0.367*4)+0.15*(0.367*3)}=5.61

Thus on average, the number of access events is estimated to be reduced by a factor of 5.61.

5.4.5. Conclusion

The clinical study described above in Example 4 coberates the results of Examples 1 and 2 in demonstrating that HealTekPatch™ is very effective in reducing the duration of postdialysis bleeding from vascular access sites of hemodialysis patients. Treatment using HealTekPatch™ proved more effective than treatment with the control material, gauze, in all of the patients tested. Use of HealTekPatch™ material resulted in a 68% reduction in the average time required achieve cessation of bleeding Use of HealTekPatch™ material also stopped bleeding in an average of 6 minutes, while the standard care (treatment with gauze) stopped bleeding in an average of 19 minutes. Moreover, the reduction in compression time was estimated to be proportionate to the reduction in numbers of vascular access complication events. Accordingly, use of HealTekPatch™ as described above, will facilitate earlier patient ambulation, reduction in vascular access complications, and increased viability and longevity of vascular access sites.

5.5. Example 5

Regression Analysis in Hemodialysis Patients

Age, gender, race, vascular access, type of anticoagulant, duration of dialysis, diabetes and hypertension were evaluated as potential covariate factors with length of compression time in a multiple regression model.

5.5.1. Materials and Methods
5.5.1.1. Patient Selection

Sixty-six hemodialysis patients were monitored to assess the time required to obtain cessation of bleeding in hemodialysis patients and estimate reductions in vascular access complications. Patients were offered the opportunity to participate in the study when they presented for routine hemodialysis. The patients monitored met the following inclusion criteria: male and female age of 18 years and above, having chronic renal failure, undergoing chronic hemodialysis, functional vascular access as confirmed by Doppler examination, and having signed an Informed Consent Form. Patient evaluations were conducted the same as described for Example 1 to ensure that patients met study inclusion criteria and to collect relevant clinical data. (See Section 5.1.2). Compression time was measured by the same methods as described in section 5.4.2 and average compression times were calculated for each patient and the patient population.

5.5.1.2. Preliminary Analyses

A preliminary screening analysis was conducted to determine the relationship between each of the above-mentioned factors and the number of vascular access events more than four months after dialysis for patients with average compression times less than 30 minutes. Three of the 66 patients are excluded: two had compression times greater than 30 minutes and one was followed for fewer than four months after dialysis. An unadjusted p-value was determined using a nonparametric test: the Wilcoxon rank-sum test for the above-mentioned factors with two levels and the Kruskal-Wallis test for factors with more than two levels. Adjusted p-values for the above-mentioned factors were based on a Poisson regression model adjusting for time on dialysis.

A second preliminary screening analysis was conducted to determine the Spearman rank correlations between continuous measured variables and the number of vascular access events more than four months after dialysis for patients with average compression times less than 30 minutes. An unadjusted p-value for the measured variables was derived from the Spearman rank correlation. (Reference: Miller R G. Beyond ANOVA, Basics of Applied Statistics. Wiley, New York, 1986). In both tables, the adjusted p-value refers to the factor tested in a Poisson regression adjusted for the time on dialysis. Continuous variables were included using a smoothing spline representation that permits arbitrary nonlinear shapes. (Reference: Hastie T J and Tibshirani R J. Generalized Additive Models Chapman and Hall, NY, 1990). Adjusted p-values were based on a Poisson smoothing spline model adjusting for time on dialysis. This model is described further below.

5.5.1.3. Multiple Regression Analysis

A multiple regression analysis was performed to describe the variation in the number of events that occur more than four months after the start of dialysis in terms of a Poisson model. The Poisson model assumes that events within groups of patients defined by the regression variables occur independently at random times over the course of the study. The Poisson models were fit as generalized linear models with a log link (Reference: McCullagh P and Nelder J A. Generalized Linear Models, 2nd ed. Chapman and Hall, NY, 1989) using the S-Plus software (StatSci, data analysis products division of MathSoft, Inc., Seattle, Wash.). The response was the number of events occurring more than four months after the start of dialysis and the number of months on dialysis beyond the initial four was used as an offset in the Poisson model formulation to adjust for time on dialysis. This offset converts the outcome to an event rate so that the log event rate=log(events/time) is a regression function of the compression time and other covariates. The expected event rate was then expressed as a sum of components due to these covariates. Since patients with longer dialysis histories were more likely to have vascular access complication events, all regression analyses were expressed in terms of event rates, the number of events per month.

The best regression function was obtained by examining each of the variables listed in Tables 1 and 2 in candidate models. Discrete factors were fit with standard dummy variable techniques. Continuous variables were examined as smoothing splines using generalized additive model methods to assess potential nonlinearities. Appropriate parametric forms of these factors were then chosen if deemed significant.

In a Poisson regression, the deviance (or −2*log likelihood) is a measure of the goodness of fit of the model. It is expected to be close to the number of degrees of freedom (the sample size N minus the number of parameters p) in a well-fit model (Reference: McCullagh P and Nelder J A. Generalized Linear Models, 2nd ed. Chapman and Hall, NY, 1989).

For given race and compression time, the model then gives that vascular access events follow a Poisson distribution with an expected event rate. The logarithm of the number of vascular access complication events per month was related to the compression time required for Blacks and non-Blacks separately by the two equations described above in Section 5.4.4.

The predicted event rates are then calculated by taking the antilogarithm of the log event rates. Standard errors for these log predicted values may be calculated as:

$$\text{standard error} = \sqrt{[\text{Var}(a) + \text{Var}(b) * T^2 + 2 * T * \text{Cov}(a,b)]}$$

where a is the intercept, b is the slope, T is the compression time, Var indicated the variance and Cov indicates the covariance. The upper and lower limits of the 95% confidence interval are then calculated from the antilogarithm of the estimate ±1.96*standard error.

5.5.2. Results

The factors for each patient, compression time, duration of dialysis in months, and number of vascular access complications are presented in Table 6. These data were then used in the preliminary analyses and multiple regression analysis.

TABLE 6

| Patient No. | Sex | Age | Race | Diabetes Hyper-Tension | Anticoag Therapy | Fistula or Graft | Compression Time | Months On Dialysis | No. of Procedures (Events) | Events/ Mos Dial |
|---|---|---|---|---|---|---|---|---|---|---|
| 24 | M | 58 | B | D | N | F | 6.1 | 37.3 | 0 | 0.000 |
| 2 | F | 72 | B |   | N | F | 6.2 | 37.5 | 0 | 0.000 |
| 65 | M | 26 | W |   | N | F | 6.6 | 20.5 | 0 | 0.000 |
| 63 | M | 68 | W |   | E | F | 6.7 | 23.4 | 0 | 0.000 |
| 56 | M | 35 | W |   | N | F | 6.7 | 41.0 | 2 | 0.049 |
| 3 | F | 81 | B | H | N | G | 6.8 | 84.5 | 0 | 0.000 |
| 20 | M | 46 | W |   | A | F | 8.3 | 73.2 | 0 | 0.000 |
| 40 | M | 77 | A | H | N | F | 8.3 | 13.6 | 0 | 0.000 |
| 7 | F | 66 | H | D/H | W | F | 9.0 | 19.6 | 0 | 0.000 |
| 44 | M | 58 | W |   | N | F | 9.2 | 13.5 | 0 | 0.000 |
| 37 | F | 68 | W |   | N | F | 9.3 | 4.1 | 0 | 0.000 |
| 47 | F | 56 | B | D | A | F | 9.3 | 17.3 | 1 | 0.058 |
| 53 | M | 63 | B | D | A | F | 9.5 | 5.1 | 0 | 0.000 |
| 41 | M | 83 | A | D | E | F | 10.0 | 16.4 | 0 | 0.000 |
| 8 | M | 65 | A | H | N | F | 10.5 | 29.5 | 1 | 0.034 |
| 50 | M | 71 | B |   | N | F | 10.5 | 18.9 | 1 | 0.053 |
| 6 | M | 75 | W |   | E | F | 10.6 | 36.2 | 1 | 0.028 |
| 17 | M | 65 | W |   | N | G | 10.6 | 35.0 | 4 | 0.114 |
| 25 | M | 38 | B |   | N | F | 10.9 | 28.6 | 1 | 0.035 |
| 9 | M | 85 | W | H/D | N | F | 11.1 | 37.3 | 1 | 0.027 |
| 62 | F | 69 | W |   | N | G | 11.5 | 46.9 | 2 | 0.043 |
| 66 | M | 68 | A | D | W | F | 11.8 | 20.9 | 1 | 0.048 |
| 22 | F | 37 | B |   | N | F | 12.0 | 31 | 3 | 0.097 |
| 52 | M | 65 | W | H | A | F | 12.2 | 27.6 | 0 | 0.000 |
| 45 | M | 56 | W | D | N | F | 12.3 | 34.5 | 0 | 0.000 |
| 54 | M | 41 | B |   | N | F | 12.3 | 11.2 | 0 | 0.000 |
| 27 | F | 49 | B | D | N | F | 12.7 | 38.7 | 0 | 0.000 |
| 16 | M | 76 | W | D | W | F | 13.3 | 9.2 | 0 | 0.000 |
| 10 | M | 84 | A |   | N | F | 14.0 | 12.5 | 1 | 0.080 |
| 58 | F | 81 | B | H | N | G | 14.1 | 24.4 | 1 | 0.041 |
| 34 | F | 63 | B | H | E | G | 14.2 | 16.7 | 0 | 0.000 |
| 35 | M | 86 | W |   | A | F | 15.2 | 8.3 | 0 | 0.000 |
| 49 | M | 87 | A | H | E | F | 15.2 | 35.5 | 0 | 0.000 |
| 61 | F | 65 | B | D | E | G | 15.2 | 13.4 | 2 | 0.149 |
| 31 | F | 48 | A |   | N | F | 15.5 | 49.2 | 1 | 0.020 |
| 55 | M | 78 | W |   | N | F | 15.8 | 23.1 | 2 | 0.087 |
| 38 | M | 60 | W |   | N | G | 15.8 | 49.2 | 3 | 0.061 |
| 42 | F | 77 | A | H | A | F | 16.0 | 38.3 | 0 | 0.000 |
| 36 | F | 40 | B |   | N | G | 16.1 | 29.7 | 3 | 0.101 |
| 15 | F | 78 | W |   | A | G | 16.2 | 27.5 | 0 | 0.000 |
| 46 | F | 31 | H |   | N | G | 16.2 | 17.4 | 0 | 0.000 |
| 57 | F | 84 | B | H | N | G | 16.3 | 42.5 | 1 | 0.024 |
| 39 | F | 76 | A | H/D | E | F | 16.7 | 16.4 | 0 | 0.000 |
| 51 | F | 86 | A |   | N | F | 16.7 | 56.0 | 4 | 0.071 |
| 12 | F | 80 | A |   | N | F | 17.1 | 51.4 | 1 | 0.019 |
| 59 | M | 55 | W | D | W | G | 17.7 | 64.5 | 3 | 0.046 |
| 4 | F | 69 | W |   | W | G | 18.3 | 41.6 | 0 | 0.000 |
| 28 | F | 84 | A |   | N | F | 18.3 | 33.5 | 1 | 0.030 |
| 33 | F | 65 | H | D | N | F | 18.5 | 40.5 | 1 | 0.025 |
| 43 | M | 40 | W | D | N | F | 18.8 | 31.6 | 2 | 0.063 |
| 26 | M | 68 | W | H | W | G | 19.1 | 31.1 | 2 | 0.064 |
| 5 | M | 63 | B | H | A | F | 20.5 | 18.4 | 0 | 0.000 |
| 14 | M | 49 | W | D | N | F | 20.5 | 39.1 | 1 | 0.026 |
| 18 | M | 65 | B | D | N | G | 20.6 | 22.8 | 2 | 0.088 |
| 21 | F | 69 | W |   | E | G | 20.8 | 27.0 | 1 | 0.037 |
| 29 | M | 73 | A |   | W | G | 21.0 | 15.7 | 2 | 0.128 |

TABLE 6-continued

| 60 | M | 48 | A | H | W | F | 22.2 | 36.3 | 1 | 0.028 |
|----|---|----|---|---|---|---|------|------|---|-------|
| 1  | M | 62 | W |   | W | G | 22.3 | 47.0 | 2 | 0.043 |
| 30 | M | 64 | B | D | N | F | 22.5 | 14.8 | 0 | 0.000 |
| 13 | F | 70 | W | D | E | G | 22.6 | 11.2 | 1 | 0.090 |
| 32 | F | 62 | B | D | W | G | 22.8 | 32.5 | 1 | 0.031 |
| 19 | F | 69 | W | D | A | F | 24.1 | 18.8 | 0 | 0.000 |
| 64 | F | 85 | B |   | W | G | 26.0 | 8.4  | 1 | 0.119 |
| 23 | F | 76 | A |   | W | F | 27.1 | 18.5 | 0 | 0.000 |
| 48 | M | 73 | W | D | N | F | 34.3 | 31.5 | 0 | 0.000 |
| 11 | M | 78 | A | D | N | F | 48.0 | 33.4 | 1 | 0.030 |

| Legend | M | Male   | B | Black    | A | Aspirin  |
|--------|---|--------|---|----------|---|----------|
|        | F | Female | W | White    | E | Ecotrin  |
|        |   |        | H | Hispanic | W | Warfarin |
|        |   |        | A | Asian    | N | None     |

The results of the preliminary analyses presented in Tables 7 and 8. Table 7 shows the effect of factors on number of vascular access events more than four months after dialysis for patients with average compression times less than 30 minutes. Table 8 shows the Spearman rank correlations between continuous measured variables and the number of vascular access events more than four months after dialysis for patients with average compression times less than 30 minutes. The results together show that only race and compression time are significant both before and after adjusting for duration of dialysis, which was a highly significant factor. Black patients and patients with longer compression times were more likely to experience vascular access complications. The adjustment for duration of dialysis had little effect on the other covariates.

TABLE 7

|                 |    | Number of Events |    |   |   |   | P-value    |          |
|-----------------|----|---|----|---|---|---|------------|----------|
|                 | N  | 0 | 1  | 2 | 3 | 4 | Unadjusted | Adjusted |
| OVERALL         | 63 | 27| 21 | 9 | 4 | 2 |            |          |
| By Gender       |    |   |    |   |   |   | 0.83       | 0.81     |
| Female          | 28 | 11| 10 | 6 | 1 | 0 |            |          |
| Male            | 35 | 16| 11 | 3 | 3 | 2 |            |          |
| By Site         |    |   |    |   |   |   | 0.42       | 0.42     |
| Fistula         | 42 | 19| 15 | 4 | 2 | 2 |            |          |
| Graft           | 21 | 8 | 6  | 5 | 2 | 0 |            |          |
| By Anticoagulant|    |   |    |   |   |   | 0.28       | 0.37     |
| A               | 8  | 3 | 4  | 1 | 0 | 0 |            |          |
| C               | 11 | 7 | 2  | 1 | 1 | 0 |            |          |
| N               | 35 | 12| 12 | 6 | 3 | 2 |            |          |
| E               | 9  | 5 | 3  | 1 | 0 | 0 |            |          |
| By Race         |    |   |    |   |   |   | 0.31       | 0.17     |
| Asian           | 15 | 6 | 6  | 1 | 2 | 0 |            |          |
| Black           | 18 | 6 | 4  | 6 | 1 | 1 |            |          |
| Hispanic        | 3  | 2 | 1  | 0 | 0 | 0 |            |          |
| White           | 27 | 13| 10 | 2 | 1 | 1 |            |          |
| By Black Race   |    |   |    |   |   |   | 0.11       | 0.04     |
| By Diabetes     |    |   |    |   |   |   | 0.32       | 0.84     |
| Yes             | 22 | 12| 5  | 3 | 1 | 1 |            |          |
| No              | 41 | 15| 16 | 6 | 3 | 1 |            |          |
| By Hypertension |    |   |    |   |   |   | 0.69       | 0.18     |
| Yes             | 15 | 6 | 7  | 2 | 0 | 0 |            |          |
| No              | 48 | 21| 14 | 7 | 4 | 2 |            |          |

TABLE 8

|                     |             | P-value    |          |
|---------------------|-------------|------------|----------|
| Variable            | Correlation | Unadjusted | Adjusted |
| Age                 | -0.07       | 0.58       | 0.36     |
| Compression Time    | 0.23        | 0.07       | 0.10     |
| Duration of Dialysis| 0.34        | 0.007      |          |

The results of the multiple Poisson regression model analysis for vascular access events more than four months after dialysis for patients with average with compression times of less than 30 minutes are presented in Table 9. The results show that only the covariates of compression time and race (Black/not Black) were significant predictors in a multiple regression model. Using a generalized additive model, a smoothing spline representation for compression time was obtained which was then approximated by a piecewise linear function such that longer compression times increased the event rate up to 11 minutes and then had no further effect. The inclusion of this piecewise function and the factor for race reduced the deviance to 60.7 on 60 degrees of freedom indicating that the remaining lack of fit could be taken as random Poisson variation. In a null model without any covariates, the deviance was 71.5 on 62 degrees of freedom showing that the counts were nearly Poisson (i.e., the events were nearly random) without any adjustment or stratification.

TABLE 9

| Variable          | Coefficient | Standard Error | P-value |
|-------------------|-------------|----------------|---------|
| Intercept         | -7.042      | 1.837          |         |
| Compression Time* | 0.367       | 0.170          | 0.03    |
| Black Race        | 0.305       | 0.133          | 0.02    |

*Compression Time is truncated at 11 minutes.
Null Deviance: 71.47239 on 62 degrees of freedom
Residual Deviance: 60.66224 on 60 degrees of freedom
Correlation of Regression Coefficients
Intercept with compression time: -0.997
Intercept with race: -0.019
Compression time with race: 0.035

The results of the logarithmic relation of the number of vascular access complication events per month to the compression time required for Blacks and non-Blacks separately indicated that, adjusting for time on dialysis, an increase of one minute in the compression time (up to 11 minutes) increased the log number of events by 0.367 (standard error=0.170) or the number of events by a factor of 44% (95% CI=3%-101%) for all patients. There was an increase of 36% (95% CI=5%-76%) for Black patients compared with non-Black patients at all compression times. There was no significant interaction between these two factors.

The results of the analyses presented herein indicate that from a practical and clinical standpoint compression times of 5 minutes of less are optimal, between 5 and 10 minutes resulted in incremental damage to the vascular access site and compressions greater than 10 minutes were damaging to the vascular access site. The relationship between compression time and vascular access complications determined using gauze alone can serve as a baseline from which to compare the methods of the invention which use a vasoconstrictor or coagulant rather than gauze or a bandage without a vasoconstrictor or coagulant.

5.6. Example 6

Use of the Healtekpatch™ to Reduce Morbidity in Hemodialysis Patients

Example 6 is also directed toward a study that measures morbidity when utilizing the HealTekPatch™ as a device to promote rapid wound closure and cessation of bleeding from such vascular access sites in hemodialysis patients following needle removal.

The study presented in Example 6 differs from that of Example 4 in several aspects, including, but not limited to, the number of hemodialysis patients in the study, the frequency of recording of compression time data, and the recording of morbidity.

5.6.1. Materials and Methods

HealTekPatch™ (Marine Polymer Technologies, Danvers, Mass.), a fully-acetylated poly-N-acetyl glucosamine (p-GlcNAc), is a highly purified polysaccharide free of protein and other contaminants (see Sections 4.1.4 and 5.1.1).

5.6.1.1. Patient Selection

Three hundred hemodialysis patients are monitored for about 30 months to one year to assess the time required to obtain cessation of bleeding in hemodialysis patients and estimate reductions in vascular access complications. Patients are offered the opportunity to participate in the study when they are presented for routine hemodialysis. The patients monitored meet the following inclusion criteria: male and female age of 18 years and above, having chronic renal failure, undergoing chronic hemodialysis, functional vascular access as confirmed by Doppler examination, and having signed an Informed Consent Form. Patient evaluations are conducted the same as described for Example 1 to ensure that patients meet study inclusion criteria and to collect relevant clinical data. (See Section 5.1.2). Compression time is measured by the same methods as described in section 5.4.2 and average compression times are calculated for each patient and the patient population.

5.6.2. Treatment Method

The treatment method is practiced the same as described in Example 4 with the exception that actual measurements of compression time to achieve hemostasis are not recorded for all 300 hemodialysis patients for each hemodialysis session (see Section 5. 4.2). Instead, for each patient, compression times are recorded at six week intervals. Death is recorded and average morbidity was calculated as a percentage of the patient population.

5.6.3. Results

For a one year study of hemdialysis patients, the expected percent morbidity is 20% where gauze alone without a coagulant or vasoconstrictor is applied, resulting in longer compression times to achieve hemostasis. For hemodialysis patients where gauze alone is used without a coagulant or vasoconstrictor is applied, resulting in longer compression times to achieve hemostasis, the 5-year survival rate is 29% of patients. The expected percent morbidity is below 20%, and the expected 5-year survival rate of patients is 30% or greater, when the methods of the invention are practiced for one year or longer.

It is apparent that many modifications and variations of this invention as set forth here may be made without departing from the spirit and scope thereof. The specific embodiments described above are given by way of example only, and the invention is limited only by the terms of the appended claims.

Various publications are cite herein, the disclosures of which are incorporated by reference in their entireties.

What is claimed:

1. A method for reducing complications at a vascular access site associated with hemodialysis therapy in a human patient at risk for said complications, said method comprising:
    a) applying topically to the skin at a site where hemodialysis needles have been removed in said patient during a hemodialysis session a barrier-forming material comprising poly-β-1→4-N-acetylglucosamine;
    b) applying compression to or proximal to the site where the hemodialysis needles have been removed for a duration of about one to about fourteen minutes; and
    c) repeating steps a) and b) for at least about 70% of hemodialysis therapy sessions;
wherein the vascular access site is a vein sutured to an artery, a native arteriovenous fistula, or a synthetic vascular graft.

2. The method of claim 1, wherein the complication is a long term vascular access complication.

3. The method of claim 2, wherein the long term vascular access complication is hyperplasia, thrombosis, venous stenosis, arterial stenosis, morbidity, or a reduction in blood flow through the vascular access site relative to a newly matured vascular access site.

4. The method of claim 1, wherein the complication is a short term vascular access complication.

5. The method of claim 4, wherein the short term vascular access complication is hematoma or infection.

6. The method of claim 1, wherein the reduction in complications is a reduction in infection rate.

7. The method of claim 6, wherein the infection is an HIV, a Hepatitis C, a vancomycin resistant enterococcus, or macrolide-lincosamide-streptogramin B ("MLS")-resistant bacterial infection.

8. A method for reducing the failure rate of a vascular access site associated with hemodialysis therapy in a human patient, said method comprising:
    a) applying topically to the skin at a site where hemodialysis needles have been removed in said patient during a hemodialysis session a barrier-forming material comprising poly-β-1→4-N-acetylglucosamine;
    b) applying compression to or proximal to the site where the hemodialysis needles have been removed for a duration of about one to about fourteen minutes; and
    c) repeating steps a) and b) for at least about 70% of hemodialysis therapy sessions,
wherein the vascular access site is a vein sutured to an artery, a native arteriovenous fistula, or a synthetic vascular graft.

9. A method for reducing the failure rate of a vascular access site associated with hemodialysis therapy in a human patient, said method comprising:
    a) applying topically to the skin at a site where hemodialysis needles have been removed in said patient during a hemodialysis session a barrier-forming material comprising poly-β-1→4-N-acetylglucosamine; and
    b) applying compression to or proximal to the site where the hemodialysis needles have been removed for a duration of about one to about fourteen minutes;
wherein the vascular access site is a vein sutured to an artery, a native arteriovenous fistula, or a synthetic vascular graft; and wherein the reduction in the failure rate of a vascular access site prolongs the use of a vascular access site by at least 1 year.

10. A method for reducing the average number of interventions to repair or replace a vascular access site associated with hemodialysis therapy in a human patient, said method comprising:
   a) applying topically to the skin at a site where hemodialysis needles have been removed in said patient during a hemodialysis session a barrier-forming material comprising poly-β-1→4-N-acetylglucosamine; and
   b) applying compression to or proximal to the site where the hemodialysis needles have been removed for a duration of about one to about fourteen minutes; and
   c) repeating steps a) and b) for at least about 70% of hemodialysis therapy sessions, wherein the vascular access site is a vein sutured to an artery, a native arteriovenous fistula, or a synthetic vascular graft.

11. The method of claim 1, 8, 9 or 10, wherein the compression is maintained for about one to about ten minutes.

12. The method of claim 1, 8, 9 or 10, wherein the compression is maintained for about one to about eleven minutes.

13. The method of claim 9, further comprising repeating steps a) and b) for at least about 70% of hemodialysis therapy sessions.

14. The method of claim 1, 8, 10, or 13, wherein the hemodialysis therapy sessions are administered for at least one month with 1 or more hemodialysis sessions a week.

15. The method of claim 1, 8 or 10, wherein said patient is a patient that requires 10 minutes or more of compression to achieve hemostasis using compression alone.

16. The method of claim 1, 8 or 10, wherein said patient has an average hemostasis time of about 18 to 21 minutes using compression alone.

17. The method of claims 1, 8 or 10, wherein the patient is an end stage renal disease patient.

18. The method of claims 1, 8 or 10, wherein the patient is older than 55 years of age.

19. The method of claims 1, 8 or 10, wherein the patient is an African American.

20. The method of claim 1, 8, or 10, wherein the vascular access site comprises a native arteriovenous fistula.

21. The method of claim 1, 8, or 10, wherein the vascular access site comprises a synthetic vascular graft.

22. The method of claim 1, 8 or 10, wherein the barrier-forming material further comprises a vasoconstrictor.

23. The method of claim 22, wherein said vasoconstrictor is adrenaline, endothelin-1, epinephrine, phenylephrine, serotonin, prostoglandin, thromboxane, norepinephrine, methergine, oxytocin, or isopreland U-46619.

24. The method of claim 1, 8 or 10, wherein the barrier-forming material further comprises a coagulant.

25. The method of claim 24, wherein said coagulant is aminohexanoic acid, a source of calcium ions, calcium alginate, calcium sodium alginate, chitin, chitosan, cyanoacrylates, epsilon-aminocaproic acid, metha-crylates, or tranexamic acid.

26. The method of claim 1, 8 or 10, wherein the barrier-forming material further comprises an anti-fungal, anti-viral, or anti-bacterial agent.

27. The method of claim 1, 8 or 10, wherein the barrier-forming material is formulated as a mat, a patch, or a gauze.

28. The method of claim 1, 8 or 10, wherein the poly-β-1→4-N-acetylglucosamine comprises at least 40% of N-acetylglucosamine monosaccharides that are acetylated.

29. The method of claim 1, 8 or 10, wherein the poly-β-1→4-N-acetylglucosamine is fully-acetylated.

30. The method of claim 1, 8 or 10, wherein the poly-β-1→4-N-acetylglucosamine comprises at least one N-acetylglucosamine monosaccharide that is deacetylated.

31. The method of claim 1, 8 or 10, wherein the poly-β-1→4-N-acetylglucosamine is derived from microalgae.

32. The method of claim 1, 8 or 10, wherein the poly-β-1→4-N-acetylglucosamine is biocompatible.

33. The method of claim 1, 8 or 10, wherein the poly-β-1→4-N-acetylglucosamine is free of protein.

34. The method of claim 1, 8 or 10, wherein said patient has an average hemostasis time of about 21 to 24 minutes using compression alone.

* * * * *